US012653867B2

(12) United States Patent
Schnecker et al.

(10) Patent No.: US 12,653,867 B2
(45) Date of Patent: *Jun. 16, 2026

(54) LYOPHILIZED RECOMBINANT VWF FORMULATIONS

(71) Applicant: Takeda Pharmaceutical Company Limited, Osaka (JP)

(72) Inventors: Kurt Schnecker, Vienna (AT); Eva Haidweger, Vienna (AT); Peter Turecek, Klosterneuberg (AT)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/514,906

(22) Filed: Oct. 29, 2021

(65) Prior Publication Data

US 2022/0257723 A1     Aug. 18, 2022

Related U.S. Application Data

(60) Division of application No. 16/258,488, filed on Jan. 25, 2019, now Pat. No. 11,197,916, and a division of application No. 16/258,490, filed on Jan. 25, 2019, now Pat. No. 11,191,813, said application No. 16/258,488 is a division of application No. 14/939,364, filed on Nov. 12, 2015, now Pat. No. 10,232,022, and a continuation of application No. 14/693,078, filed on Apr. 22, 2015, now Pat. No. 11,191,837, said application No. 16/258,490 is a continuation of application No. 14/693,078, filed on Apr. 22, 2015, now Pat. No. 11,191,837, said application No. 14/939,364 is a continuation of application No. 12/603,064, filed on Oct. 21, 2009, now abandoned, said application No. 14/693,078 is a continuation of application No. 12/342,646, filed on Dec. 23, 2008, now abandoned.

(60) Provisional application No. 61/107,273, filed on Oct. 21, 2008, provisional application No. 61/017,881, filed on Dec. 31, 2007, provisional application No. 61/017,418, filed on Dec. 28, 2007.

(51) Int. Cl.

| | |
|---|---|
| *A61K 38/36* | (2006.01) |
| *A61K 9/08* | (2006.01) |
| *A61K 9/19* | (2006.01) |
| *A61K 38/16* | (2006.01) |
| *A61K 38/17* | (2006.01) |
| *A61K 47/12* | (2006.01) |
| *A61K 47/18* | (2017.01) |
| *A61K 47/22* | (2006.01) |
| *A61K 47/26* | (2006.01) |
| *A61P 7/04* | (2006.01) |

(52) U.S. Cl.
CPC ................ *A61K 38/36* (2013.01); *A61K 9/08* (2013.01); *A61K 9/19* (2013.01); *A61K 38/16* (2013.01); *A61K 38/17* (2013.01); *A61K 47/12* (2013.01); *A61K 47/183* (2013.01); *A61K 47/22* (2013.01); *A61K 47/26* (2013.01)

(58) Field of Classification Search
CPC ............ A61K 38/36; A61K 9/08; A61K 9/19; A61K 38/16; A61K 38/17; A61K 47/12; A61P 7/04
See application file for complete search history.

(56) References Cited

U.S. PATENT DOCUMENTS

| | | | |
|---|---|---|---|
| 3,941,763 A | 3/1976 | Sarantakis | |
| 5,670,132 A | 9/1997 | Griffiths et al. | |
| 5,854,403 A * | 12/1998 | Fischer | ................ C07K 14/755 |
| | | | 530/416 |
| 5,869,617 A | 2/1999 | Fischer et al. | |
| 5,872,099 A | 2/1999 | Fischer et al. | |
| 5,892,005 A | 4/1999 | Fischer et al. | |
| 5,900,476 A | 5/1999 | Ruggeri et al. | |
| 5,925,738 A | 7/1999 | Miekka et al. | |
| 6,005,007 A | 12/1999 | Farmer et al. | |
| 6,005,077 A | 12/1999 | Schwarz et al. | |
| 6,040,143 A | 3/2000 | Venta et al. | |
| 6,103,693 A | 8/2000 | Fischer et al. | |
| 6,267,958 B1 | 7/2001 | Andya et al. | |
| 6,310,183 B1 | 10/2001 | Johannessen et al. | |
| 6,465,624 B1 | 10/2002 | Fischer et al. | |
| 6,531,577 B1 | 3/2003 | Kaersgaard et al. | |
| 6,579,723 B1 * | 6/2003 | Mitterer | .............. C07K 14/755 |
| | | | 422/534 |
| 6,649,386 B2 | 11/2003 | Roser | |
| 6,875,432 B2 | 4/2005 | Liu et al. | |
| 6,953,837 B2 | 10/2005 | Mitterer et al. | |

(Continued)

FOREIGN PATENT DOCUMENTS

| | | |
|---|---|---|
| CA | 2301514 A1 | 3/1999 |
| EP | 1314437 A1 | 5/2003 |

(Continued)

OTHER PUBLICATIONS

Yampolsky et al., "The Exchangeability of Amino Acids in Proteins," Genetics, 2005, 170: 1459-1472. (Year: 2005).*
Akers et al., Peptides and proteins as parenteral solutions, Chapter 8, IN: Frokjaer et al. (eds), Pharmaceutical Formulation Development of Peptides and Proteins, CRC Press (2000).
Baxter International Inc. & Baxter Healthcare SA, Australian Patent Application 2008345135 (2008).

(Continued)

*Primary Examiner* — Julie Ha
(74) *Attorney, Agent, or Firm* — Morgan, Lewis & Bockius LLP

(57) ABSTRACT

The present invention provides long-term stable pharmaceutical formulations of lyophilized recombinant von-Willebrand Factor (rVWF) and methods for making and administering said formulations.

16 Claims, 3 Drawing Sheets
Specification includes a Sequence Listing.

(56) References Cited

U.S. PATENT DOCUMENTS

| 7,005,502 | B1 | 2/2006 | Schwarz et al. |
| 7,049,336 | B2 | 5/2006 | Walther et al. |
| 7,166,709 | B2 | 1/2007 | Josic et al. |
| 7,220,836 | B2 | 5/2007 | Roser |
| 7,244,824 | B2 | 7/2007 | Roser |
| 7,244,825 | B2 | 7/2007 | Roser |
| 7,659,247 | B2 | 2/2010 | Kretschmar et al. |
| 7,833,766 | B2 | 11/2010 | Zhu et al. |
| 7,888,476 | B2 | 2/2011 | Martel et al. |
| 7,932,355 | B2 | 4/2011 | Chtourou et al. |
| 7,956,160 | B2 | 6/2011 | Krishnan et al. |
| 7,960,182 | B2 | 6/2011 | Betley et al. |
| 8,187,799 | B2 | 5/2012 | Tsvetkova et al. |
| 8,354,505 | B2 | 1/2013 | Ristol Debart et al. |
| 8,597,910 | B1 | 12/2013 | Ginsburg et al. |
| 2001/0046487 | A1 | 11/2001 | Roser et al. |
| 2002/0019036 | A1 | 2/2002 | Schwarz et al. |
| 2003/0138913 | A1 | 7/2003 | Josic et al. |
| 2004/0038878 | A1 | 2/2004 | Tanikawa et al. |
| 2005/0074866 | A1 | 4/2005 | Grancha et al. |
| 2006/0008415 | A1 | 1/2006 | Kaisheva et al. |
| 2006/0160948 | A1 | 7/2006 | Scheiflinger et al. |
| 2007/0021338 | A1 | 1/2007 | Hansen et al. |
| 2008/0234193 | A1* | 9/2008 | Bossard .................... A61P 7/00 |
| | | | 514/17.2 |
| 2009/0088370 | A1 | 4/2009 | Winge |
| 2009/0148406 | A1 | 6/2009 | Jezek |
| 2009/0192076 | A1 | 7/2009 | Matthiessen et al. |
| 2009/0264494 | A1* | 10/2009 | D'Mello .............. C07D 409/06 |
| | | | 514/414 |
| 2010/0028372 | A1 | 2/2010 | Jezek |
| 2010/0092566 | A1 | 4/2010 | Alessi et al. |
| 2010/0137211 | A1 | 6/2010 | Monahan et al. |
| 2010/0305305 | A1 | 12/2010 | Poulle |
| 2011/0092681 | A1 | 4/2011 | Mitterer et al. |
| 2011/0112023 | A1 | 5/2011 | Dickneite et al. |
| 2012/0027740 | A1 | 2/2012 | Philippart |
| 2012/0027743 | A1 | 2/2012 | Jiang et al. |

FOREIGN PATENT DOCUMENTS

| EP | | 1522312 | A1 | 4/2005 |
| EP | | 1522312 | B1 | 4/2005 |
| EP | | 1632501 | A1 | 3/2006 |
| EP | | 1037923 | B9 | 5/2006 |
| WO | WO 1986/006096 | A1 | 10/1986 |
| WO | WO 1993/000107 | A1 | 1/1993 |
| WO | WO 1993/016709 | A1 | 9/1993 |
| WO | WO 1996/022107 | A1 | 7/1996 |
| WO | WO 1997/004801 | A1 | 2/1997 |
| WO | WO 1997/018834 | A1 | 5/1997 |
| WO | WO 1998/003683 | A1 | 1/1998 |
| WO | WO 1998/022135 | A1 | 5/1998 |
| WO | WO 2002/029025 | A2 | 4/2002 |
| WO | WO 2004/000366 | A1 | 12/2003 |
| WO | WO 2004/039337 | A2 | 5/2004 |
| WO | WO 2005/040214 | | 5/2005 |
| WO | WO 2008/151817 | A1 | 12/2008 |
| WO | WO 2009/086400 | A2 | 7/2009 |
| WO | WO 2009082648 | A1 | 7/2009 |

OTHER PUBLICATIONS

Baxter International Inc. & Baxter Healthcare SA, Australian Patent Application 2008345135, A Figure 3 from the patent Application distinguishing the citrate and Advate 1 :3 formulation data (2008).
Baxter International Inc. & Baxter Healthcare SA, Australian Patent Application 2008345135, Amended Claims, dated Dec. 22, 2014.
Baxter International Inc. & Baxter Healthcare SA, Australian Patent Application 2008345135, Contents table to the Patent Application (2008).
Berendsen et al., A Glimpse of the Holy Grail? Science, 282: 642-3 (1998).*.

Brody, Lawrence C., "Hybridization," https://www.genome.gov/genetics-glossary/hybridization, pp. 1-3. Accessed Apr. 15, 2020. (Year : 2020).
Bradley et al., Limits of cooperativity in a structurally modular protein: Response of the notch ankyrin domain to analogous alanine substitutions in each repeat. J. Mol. Biol., 324: 373-86 (2002).*.
Brunner, Facts and arguments—Opposition against EP 2349314 (2013).
Budde et al., Comparative Analysis and Classification of von Willebrand Factor/Factor VIII Concentrates: Impact on Treatment of Patients with von Willebrand Disease, Semin. Thromb. Hemost, 32(6):626-35 (2006).
Carpenter et al., Interactions of stabilizing additives with proteins during freeze-thawing and freeze-drying, Dev. Biol. Stand., 74: 225-38 (1992).
Chang et al., Development of a stable freeze-dried formulation of recombinant human interleukin-1 receptor antagonist, Pharm. Res., 13: 243-9 (1996).
Chang et al., Surface-induced denaturation of proteins during freezing and its inhibition by surfactants, J. Pharm. Sci., 85: 1325-30 (1996).
Chen et al., Influence of calcium ions on the structure and stability of recombinant human deoxyribonuclease I in the aqueous and lyophilized states, J. Pharm. Sci., 88: 477-82 (1999).
Chen et al., Influence of histidine on the stability and physical properties of a fully human antibody in aqueous and solid forms, Pharm. Res., 20: 1952-60 (2003).
Chen, Formulation concerns of protein drugs. Drug Dev. Indust. Pharm. 18(11 &12):1311-54 (1992).
Curriculum vitae of Thomas Exner dated Nov. 25, 2014.
Davis et al., Preparation and characterization of antibodies with specificity for the amino-terminal tetrapeptide sequence of the platelet-derived connective tissue activating peptide-I II, Biochem. Int., 10: 394-414 (1985).
Declaration of Emmanuel Favalaoro dated May 4, 2015.
Declaration of Jeffrey Hey dated Jul. 13, 2015.
Declaration of Thomas Exner dated May 6, 2015.
Definition of derivative and analog from nttgJ/cancerweb.ncl.ac.uk/omd/about.11tml. pp: 1-5. Accessed Jul. 7, 2005.*.
Derrick et al., Effect of metal cations on the conformation and inactivation of recombinant human factor Viii, J. Pharm. Sci., 93: 2549-57 (2004).
Designing Custom peptides, SIGMA Genosys, pp. 1-3. Accessed Dec. 16, 2004. *.
Dr. Emmanuel Favaloro, Diagnostic Haemostasis Laboratory/Haemostasis and Thrombosis Research Unit, Haematology, ICPMR, Westmead Hospital Curriculum vitae (Abridged) dated Nov. 25, 2014.
Entry for Recombinate®, in MIMS Annual 2007.
Erickson et al., Solid-phase peptide synthesis, IN: The Proteins, 3rd ed., 2: 257-527 (1976).
European Search Report and Written Opinion issued in connection with European Patent Application No. 13 15 0822, dated May 13, 2013.
Exner et al., Interactions of Factor VII with vWF in Mixed Immunoradiometric Assay Systems, in Factor VII—von Willebrand Factor, Biochemical. Methodological, and Functional Aspects, 1 (12) :227-53 (1989).
Exner, Comparison of Commercially Available Products (2015).
Fatouros et al., Recombinant factor VIII SQ-influence of oxygen, metal ions, pH and ionic strength on its stability in aqueous solution, Int. J. Pharm., 155: 121-31 (1997).
Fernandes et al.; Polysialylated asparaginase: Preparation, activity and pharmacokinetics. Biochim. Biophys. Acta 1341: 26-34 (1997).
Finn et al., The synthesis of peptides by solution methods with emphasis on peptide hormones, IN: The Proteins, 3rd ed., 2: 105-253 (1976).
Fischer et al., Structural analysis of recombinant von Willebrand factor produced at industrial scale fermentation of transformed CHO cells co-expressing recombinant furin, FEBS Let., 375:259-62 (1995).

(56)　　　　　References Cited

OTHER PUBLICATIONS

Fischer et al., Structural analysis of recombinant von Willebrand factor: identification of hetero-and homo-dimers, FEBS Let., 351: 345-8 (1994).

Fransson, Oxidation of human insulin-like growth factor I in formulation studies. 3. Factorial experiments of the effects of ferric ions, EDTA, and visible light on methionine oxidation and covalent aggregation in aqueous solution, J. Pharm. Sci., 86: 1046-50 (1997).

Furuya et al., Implementation of a 20-nm pore-size filter in the plasma-derived factor VIII manufacturing process. Vax Sanguinis, 91: 119-25 (2006).

Gen Bank accession No. NM_000543, *Homo sapiens* sphingomyelin phosphodiesterase 1, acid lysosomal (SMPD1), transcript variant ASM-1, mRNA, Mar. 29, 2009.

GenBank accession No. NM_000552, *Homo sapiens* von Willebrand factor (VWF), mRNA, Mar. 29, 2009.

Ginsburg, Human von Willebrand Factor (VWF): Isolation of Complementary DNA (cDNA) Clones and Chromosomal Localization, Science, vol. 228, No. 4706, Jun. 21, 1985, pp. 1401-1406.

Glycine is a natural product, from www.beniamin-rn,:Is.com/d1ernistry/arnino-acids.htrn, pp. 1-4. Accessed Apr. 9, 2014.

Gokarn et al., Excipients for Protein Drugs, Excipient Development for Pharmaceutical, Biotechnology, and Drug Delivery Systems, Chapter 17, pp. 391-332 (2006).

Heller et al., Conformational stability of lyophilized PEGylated proteins in a phase-separating system, J. Pharm. Sci., 88(1 ):58-64 (1999).

Hematol J. 2000; 1 (2):72-6. "Choice of replacement therapy for hemophilia: recombinant products only?" Mannucci PM, Giangrande PL.

Highlights of Prescribing Information, Advate®, Antihemophilic Factor (Recombinant), Plasma/Albumin-Free Method, dated Jul. 2012.

Highlights of Prescribing Information, Wilate®, von Willebrand Factor/Coagulation Factor VIII Complex (Human) (Dec. 2009), with extract from ARTG register (May 20, 2013).

Hollander-Rodriguez et al., Hyperkalemia, Am. Fam. Physician, 73: 283-90 (2006).

International Search Report and Written Opinion of the International Searching Authority issued in connection with International Application No. PCT/US2008/88201, European Patent Office, dated Aug. 28, 2009.

International Search Report and Written Opinion of the International Searching Authority issued in connection with International Application No. PCT/US2008/88005, dated Mar. 7, 2009.

International Search Report and Written Opinion of the International Searching Authority issued in connection with International Application No. PCT/US2009/0614 70, European Patent Office, dated Jun. 30, 2011.

Jeffery Hey, Curriculum vitae dated Jul. 13, 2015.

Kappelgaard et al., Liquid growth hormone: Preservatives and buffers, Harm. Res., 62(Suppl 3): 98-103 (2004).

Kasper et al., Registry of Clotting Factor Concentrates (2006).

Keane, Federal court practice notice titled Expert Witnesses in Proceedings in the Federal Court of Australia, dated Aug. 1, 2011.

Kroner et al., Expressed Full-Length von Willebrand Factor Containing Missense Mutations Linked to Type IIB von Willebrand Disease Shows Enhanced Binding to Platelets, Blood, vol. 79, No. 8, Apr. 15, 1992, pp. 2048-2055.

Lam et al., Antioxidants for prevention of methionine oxidation in recombinant monoclonal antibody HER2, J. Pharm. Sci., 86: 1250-5 (1997).

Lankhof et al., von Willebrand factor without the A2 domain is resistant to proteolysis, Thromb. Haemost., 77: 1008-13 (1997).

Laursen et al., Pain perception after subcutaneous injections of media containing different buffers, Basic Clin. Pharmaco/. Toxico/., 98: 218-21 (2006).

Lecithin is a natural product, from www.,sc.org/ci1em!stry_worlrJ/issues/2003!, ulyiamQi1:les.asQ, pp. 1-7. Accessed Sep. 10, 2014.

Leyte et al., The pro-polypeptide of von Willebrand factor is required for the formation of a functional factor VIII-binding site on mature von Willebrand factor, Biochem. J., 274:257-61 (1991).

MacKenzie, Non-equilibrium freezing behaviour of aqueous systems, Phi/as. Trans. R Soc. Land B Biol. Sci., 278: 167-89 (1977).

Mannitol is a natural product, from www.sweetenerboo~Lcomimann:t0U1t1m, pp. 1-3. Accessed Sep. 10, 2014.

Ngo et al., Computational complexity, protein structure prediction, and the Levinthal Paradox, The Protein Folding Problem and Tertiary Structure Prediction, K. Mere Jr. and S. Le Grand Edition, pp. 491-495 (1994).*

Mannucci et al., Choice of replacement therapy for hemophilia: recombinant products only? Hematol. J., 1 :72-6 (2000).

Merrifield, Solid phase peptide synthesis. I.The synthesis of a tetrapeptide, J. Am. Chem. Soc., 85:2149-54 (1963).

Merrifield, Solid-phase peptide synthesis, pp. 335-361, IN: Zervas et al. (eds.), The Chemistry of Polypeptides: Essays in Honor of Dr. Leonidas Ze, vas (1973).

Migneault et al., Glutaraldehyde: behavior in aqueous solution, reaction with proteins, and application to enzyme crosslinking, Biotechniques, 37:790-6 (2004).

Minogue et al., Bacteriostatic saline containing benzyl alcohol decreases the pain associated with the injection of propofol, Anesth. Analg., 100:683-6 (2005).

Mounier et al., Arachidonic acid release from mammalian cells transfected with human groups IIA and X secreted phospholipase A(2) occurs predominantly during the secretory process and with the involvement of cytosolic phospholipase A(2)-alpha. J. Biol. Chem., 279(24): 25024-38 (2004).

Nail et al., Fundamentals of Freeze-Drying, 281-360 (2002).

Nayer et al., High Throughput Formulation: Strategies for Rapid Development of Stable Protein Products, Rational Design of Stable Protein Formulations, 177-198 (2002).

Notification from Australian Patent Office of submission of observations against Australian Patent Application No. 2009307648, dated Jun. 11, 2013.

Notification from Australian Patent Office of submission of observations against Australian Patent Application No. 2009307648, dated May 21, 2013.

Package insert for Alphanate® with entry from US Food and Drug Administration website showing approval of product, Jan. 2007.

Package insert for Humate-P®, Antihemophilic Factor/von Willebrand Factor Complex (Human), Dried, Pasteurized, dated Oct. 2007.

Package insert for Wilate, von Willebrand Factor/Coagulation Factor VIII Complex (Human), with extract from ARTG register, dated Sep. 26, 2007.

Passot et al., Physical characterisation of formulations for the development of two stable freezedried proteins during both dried and liquid storage. Eur. J. Pharm. Biopharm., 60(3): 335-48 (2005).

Pietu et al., Production in *Escherichia coli* of a biologically active subfragment of von Willebrand factor corresponding to the platelet glycoprotein Ib, collagen and heparin binding domains. Biochem. Biophys. Res. Commun. 164:1339-47 (1989).

Plaimauer et al., Recombinant von Willebrand Factor: Preclinical development. Sem. Thromb. Hemostasis, 27: 395-403 (2001).

Powell et al., Compendium of Excipients fir Parenteral Formulations, PDA J. Pharm. Sci. Technol. 52:238-311 (1998).

Product information for Advate®, Antihemophilic Factor (Recombinant), Plasma/Albumin-Free Method, 2003.

Product information sheet for Advate®, dated Jul. 2007.

Product information sheet for Alphanate® and sale thereof, dated Jan. 2007.

Product information sheet for Innobranduo® and sale thereof, dated Aug. 10, 2004.

Product information sheet for Wilate® and sale thereof, dated Jan. 17, 2007.

Product information sheet for Wilfactin® and sale thereof, dated Jan. 16, 2006.

Randolph et al., Surfactant-protein interactions, Pharm. BiotechnoL, 13:159-75 (2002).

Registry of Clotting Factor Concentrates, 2006.

(56) References Cited

OTHER PUBLICATIONS

*Remington's Pharmaceutical Sciences*, 18th ed., Easton, Pa: Mack Publishing Co., pp. 1435-1712 (1995).

Remmele et al., Interleukin-1 receptor (IL-1 R) liquid formulation development using differential scanning calorimetry, Pharm. Res., 200-8 (1998).

Remmele et al., Minimization of recombinant human Flt3 ligand aggregation at the Tm plateau: a matter of thermal reversibility, Biochemistry, 38:5241-7 (1999).

Revised Full Prescribing Information for Antihemophilic Factor/ von Willebrand Factor Complex (Human), AlphanateO—Clean Copy, received by Australian Patent Office in connection with Australian Patent Application No. 2009307648 on May 20, 2013.

Roser et al., Trehalose drying: A novel replacement for freeze-drying. BioPharm, 4(8): 47-53 (1991).

Roy et al., Effects of benzyl alcohol on aggregation of recombinant human interleukin-1-receptor antagonist in reconstituted lyophilized formulations, J. Pharm. Sci., 94:382-96 (2005).

Rudinger et al., Characteristics of the amino acids as components of a peptide hormone sequence, Peptide Hormones, Parsons (Ed.), University Park Press, pp. 1-7, Jun. 1976. *.

Ruggeri et al., von Willebrand factor, FASEB J., (7): 308-16 (1993).

Sadler, von Willebrand factor: two sides of a coin, J. Thromb. Haemost, 3:1702-9 (2005).

Saenko et al., Strategies towards a longer acting factor VIII, Haemophilia, 12 Suppl 3: 42-51 (2006).

Salder et al., Update on the pathophysiology and classification of von Willebrand disease: a report of the subcommittee on von Willebrand factor. J. Thromb. Haemost., 4:2103-14 (2006).

Sambrook et al. (eds.), Molecular Cloning a Laboratory Manual, 2nd ed., Cold Spring Harbor Laboratory Press, pp. 9.4 7-9.51 (1989).

Schinzel et al., The phosphate recognition site of *Escherichia coli* maltodextrin phosphorylase. FESS, 286(1,2): 125-8 (1991).*.

Stewart et al., Solid Phase Peptide Synthesis, San Francisco: W.H. Freeman and Company (1969).

Submission of Observations under Section 27 in connection with Australian Patent Application No. 2009307648, dated Jun. 7, 2013.

Submission of Observations under Section 27 in connection with Australian Patent Application No. 2009307648, dated May 8, 2013.

Tang et al., Design of freeze-drying processes for pharmaceuticals: practical advice, Pharm. Res., 21 :191-200 (2004).

NCBI GenBank Accession No. CAA27972, Jan. 9, 1998.

Parti, et al., Stability of lyophilized and reconstituted plasma/ albumin-free recombinant human factor VIII (Advate rAHF-PFM). Oct. 2005; Haemophilia 11(5):492-6.

Third Party Observations in connection with European Patent No. EP 2244814, dated Aug. 16, 2013.

Tomita et al., Sensitized photooxidation of histidine and its derivatives. Products and mechanism of the reaction, Biochemistry, 8:5149-60 (1969).

Turecek et al., Evidence for Extracellular Processing of Pro-von Willebrand Factor After Infusion in Animals With and Without Severe von Willebrand Disease, Blood, vol. 94, No. 5, Sep. 1, 1999, pp. 1637-1647.

Turecek et al., Structure and Function of a Recombinant von Willebrand Factor Drug Candidate, Semin Thromb Hemost, vol. 36, No. 5, Jul. 15, 2010, pp. 510-521.

Voet et al., Biochemistry, Second Edition, John Wiley & Sons, Inc. pp. 235-41 (1995).*.

Water is natural product, from W\Atw.b,ologv-on::ne.org/dict:onary/ VVater, pp. 1-3. Accessed Apr. 24, 2014.

White et al., Factor VIII gene and hemophilia A, Blood, vol. 73, No. 1, Jan. 1989: pp. 1-12.

Wilfactin® (Wilfact®), Human von Willebrand factor, product information sheet (2006).

Yee et al., Avon Willebrand factor fragment containing the D'D3 domains is sufficient to stabilize coagulation factor VIII in mice, Blood, vol. 124, No. 3, Jul. 17, 2014, pp. 445-452.

Yin et al., Effects of antioxidants on the hydrogen peroxide-mediated oxidation of methionine residues in granulocyte colony-stimulating factor and human parathyroid hormone fragment 13-34, Pharm. Res., 21 :2377-83 (2004).

* cited by examiner

Residual moisture 2-8°C

SEQUENCE LISTING

```
<160> NUMBER OF SEQ ID NOS: 3

<210> SEQ ID NO 1
<211> LENGTH: 8833
<212> TYPE: DNA
<213> ORGANISM: Homo sapiens

<400> SEQUENCE: 1
agctcacagc tattgtggtg ggaaagggag ggtggttggt ggatgtcaca gcttgggctt        60
tatctccccc agcagtgggg actccacagc ccctgggcta cataacagca agacagtccg       120
gagctgtagc agacctgatt gagcctttgc agcagctgag agcatggcct agggtgggcg       180
gcaccattgt ccagcagctg agtttcccag ggaccttgga gatagccgca gccctcattt       240
gcaggggaag atgattcctg ccagatttgc cggggtgctg cttgctctgg ccctcatttt       300
gccagggacc ctttgtgcag aaggaactcg cggcaggtca tccacggccc gatgcagcct       360
tttcggaagt gacttcgtca acacctttga tgggagcatg tacagctttg cgggatactg       420
cagttacctc ctggcagggg gctgccagaa acgctccttc tcgattattg gggacttcca       480
gaatggcaag agagtgagcc tctccgtgta tcttgggga tttttttgaca tccatttgtt       540 tgtcaatggt accgtgacac aggggggacca aagagtctcc atgccctatg cctccaaagg       600
gctgtatcta gaaactgagg ctgggtacta caagctgtcc ggtgaggcct atggctttgt       660
ggccaggatc gatggcagcg gcaactttca agtcctgctg tcagacagat acttcaacaa       720
gacctgcggg ctgtgtggca actttaacat ctttgctgaa gatgacttta tgacccaaga       780
agggaccttg acctcggacc cttatgactt tgccaactca tgggctctga gcagtggaga       840
acagtggtgt gaacgggcat ctcctcccag cagctcatgc aacatctcct ctggggaaat       900
gcagaagggc ctgtgggagc agtgccagct tctgaagagc acctcggtgt ttgcccgctg       960 ccacctctg tggaccccg agcctttgt ggccctgtgt gagaagactt tgtgtgagtg     1020
tgctgggggg ctggagtgcg cctgccctgc cctcctggag tacgcccgga cctgtgccca     1080
ggagggaatg gtgctgtacg gctggaccga ccacagcgcg tgcagcccag tgtgccctgc     1140
tggtatggag tataggcagt gtgtgtcccc ttgcgccagg acctgccaga gcctgcacat     1200
caatgaaatg tgtcaggagc gatgcgtgga tggctgcagc tgccctgagg gacagctcct     1260
ggatgaaggc ctctgcgtgg agagcaccga gtgtccctgc gtgcattccg gaaagcgcta     1320
ccctcccggc acctccctct ctcgagactg caacacctgc atttgccgaa acagccagtg     1380
gatctgcagc aatgaagaat gtccagggga gtgccttgtc acaggtcaat cacacttcaa     1440
gagctttgac aacagatact tcaccttcag tgggatctgc cagtacctgc tggcccggga     1500
ttgccaggac cactccttct ccattgtcat tgagactgtc cagtgtgctg atgaccgcga     1560
cgctgtgtgc acccgctccg tcaccgtccg gctgcctggc ctgcacaaca gccttgtgaa     1620
actgaagcat ggggcaggag ttgccatgga tggccaggac gtccagctcc ccctcctgaa     1680
```

-continued

```
aggtgacctc cgcatccagc atacagtgac ggcctccgtg cgcctcagct acggggagga    1740
cctgcagatg gactgggatg ccgcgcggag gctgctggtg aagctgtccc ccgtctatgc    1800
cgggaagacc tgcggcctgt gtgggaatta caatggcaac cagggcgacg acttccttac    1860
cccctctggg ctggcggagc cccgggtgga ggacttcggg aacgcctgga agctgcacgg    1920
ggactgccag gacctgcaga agcagcacag cgatccctgc gccctcaacc cgcgcatgac    1980
caggttctcc gaggaggcgt gcgcggtcct gacgtccccc acattcgagg cctgccatcg    2040
tgccgtcagc ccgctgccct acctgcggaa ctgccgctac gacgtgtgct cctgctcgga    2100
cggccgcgag tgcctgtgcg gcgccctggc cagctatgcc gcggcctgcg cggggagagg    2160
cgtgcgcgtc gcgtggcgcg agccaggccg ctgtgagctg aactgcccga aaggccaggt    2220
gtacctgcag tgcgggaccc cctgcaacct gacctgccgc tctctctctt acccggatga    2280
ggaatgcaat gaggcctgcc tggagggctg cttctgcccc ccagggctct acatggatga    2340
gaggggggac tgcgtgccca aggcccagtc cccctgttac tatgacggtg agatcttcca    2400
gccagaagac atcttctcag accatcacac catgtgctac tgtgaggatg gcttcatgca    2460
ctgtaccatg agtggagtcc ccggaagctt gctgcctgac gctgtcctca gcagtcccct    2520
gtctcatcgc agcaaaagga gcctatcctg tcggcccccc atggtcaagc tggtgtgtcc    2580
cgctgacaac ctgcgggctg aagggctcga gtgtaccaaa acgtgccaga actatgacct    2640
ggagtgcatg agcatgggct gtgtctctgg ctgcctctgc cccccgggca tggtccggca    2700
tgagaacaga tgtgtggccc tggaaaggtg tccctgcttc catcagggca aggagtatgc    2760
ccctggagaa acagtgaaga ttggctgcaa cacttgtgtc tgtcgggacc ggaagtggaa    2820
ctgcacagac catgtgtgtg atgccacgtg ctccacgatc ggcatggccc actacctcac    2880
cttcgacggg ctcaaatacc tgttccccgg ggagtgccag tacgttctgg tgcaggatta    2940
ctgcggcagt aaccctggga cctttcggat cctagtgggg aataagggat gcagccaccc    3000
ctcagtgaaa tgcaagaaac gggtcaccat cctggtggag ggaggagaga ttgagctgtt    3060
tgacggggag gtgaatgtga agaggcccat gaaggatgag actcactttg aggtggtgga    3120
gtctggccgg tacatcattc tgctgctggg caaagccctc tccgtggtct gggaccgcca    3180
cctgagcatc tccgtggtcc tgaagcagac ataccaggag aaagtgtgtg gcctgtgtgg    3240
gaattttgat ggcatccaga caatgacct caccagcagc aacctccaag tggaggaaga    3300
ccctgtggac tttgggaact cctggaaagt gagctcgcag tgtgctgaca ccagaaaagt    3360
gcctctggac tcatcccctg ccacctgcca taacaacatc atgaagcaga cgatggtgga    3420
ttcctcctgt agaatcctta ccagtgacgt cttccaggac tgcaacaagc tggtggaccc    3480
cgagccatat ctggatgtct gcatttacga cacctgctcc tgtgagtcca ttggggactg    3540
cgcctgcttc tgcgacacca ttgctgccta tgcccacgtg tgtgcccagc atggcaaggt    3600
ggtgacctgg aggacggcca cattgtgccc ccagagctgc gaggagagga atctccggga    3660
gaacgggtat gagtgtgagt ggcgctataa cagctgtgca cctgcctgtc aagtcacgtg    3720
tcagcaccct gagccactgg cctgccctgt gcagtgtgtg gagggctgcc atgcccactg    3780
ccctccaggg aaaatcctgg atgagctttt gcagacctgc gttgaccctg aagactgtcc    3840
agtgtgtgag gtggctggcc ggcgttttgc ctcaggaaag aaagtcacct tgaatcccag    3900
tgaccctgag cactgccaga tttgccactg tgatgttgtc aacctcacct gtgaagcctg    3960
ccaggagccg ggaggcctgg tggtgcctcc cacagatgcc ccggtgagcc ccaccactct    4020
gtatgtggag gacatctcgg aaccgccgtt gcacgatttc tactgcagca ggctactgga    4080
```

```
cctggtcttc ctgctggatg gctcctccag gctgtccgag gctgagtttg aagtgctgaa    4140
ggcctttgtg gtggacatga tggagcggct gcgcatctcc cagaagtggg tccgcgtggc    4200
cgtggtggag taccacgacg gctcccacgc ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc gccctgaagc    4380
ctcccgcatc accctgctcc tgatggccag ccaggagccc caacggatgt cccggaactt    4440
tgtccgctac gtccagggcc tgaagaagaa gaaggtcatt gtgatcccgg tgggcattgg    4500
gccccatgcc aacctcaagc agatccgcct catcgagaag caggccctg agaacaaggc    4560 cttcgtgctg agcagtgtgg atgagctgga gcagcaaagg gacgagatcg ttagctacct    4620
ctgtgacctt gcccctgaag cccctcctcc tactctgccc cccgacatgg cacaagtcac    4680
tgtgggcccg gggctcttgg gggtttcgac cctggggccc aagaggaact ccatggttct    4740
ggatgtggcg ttcgtcctgg aaggatcgga caaaattggt gaagccgact tcaacaggag    4800
caaggagttc atggaggagg tgattcagcg gatggatgtg ggccaggaca gcatccacgt    4860
cacggtgctg cagtactcct acatggtgac tgtggagtac cccttcagcg aggcacagtc    4920
caaaggggac atcctgcagc gggtgcgaga gatccgctac cagggcggca acaggaccaa    4980
cactgggctg gccctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggccctaatg ccaacgtgca    5160
ggagctggag aggattggct ggcccaatgc ccctatcctc atccaggact ttgagacgct    5220
cccccgagag gctcctgacc tggtgctgca gaggtgctgc tccggagagg ggctgcagat    5280
ccccacccct ccccctgcac ctgactgcag ccagcccctg gacgtgatcc ttctcctgga    5340
tggctcctcc agtttcccag cttcttattt tgatgaaatg aagagtttcg ccaaggcttt    5400
catttcaaaa gccaatatag ggcctcgtct cactcaggtg tcagtgctgc agtatggaag    5460
catcaccacc attgacgtgc catggaacgt ggtcccggag aaagcccatt gctgagcct    5520 tgtggacgtc atgcagcggg agggaggccc cagccaaatc ggggatgcct tgggctttgc    5580
tgtgcgatac ttgacttcag aaatgcatgg tgccaggccg ggagcctcaa aggcggtggt    5640
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggcccagcag gcgactccaa cgtggtgaag ctccagcgaa tcgaagacct    5820
ccctaccatg gtcaccttgg gcaattcctt cctccacaaa ctgtgctctg gatttgttag    5880
gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cggggggctga ggccttcgtg ccctaacagc cagtcccctg ttaaagtgga    6060
agagacctgt ggctgccgct ggacctgccc ctgcgtgtgc acaggcagct ccactcggca    6120
catcgtgacc tttgatgggc agaatttcaa gctgactggc agctgttctt atgtcctatt    6180
tcaaaacaag gagcaggacc tggaggtgat tctccataat ggtgcctgca gccctggagc    6240
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catggaagtc aacgtttatg gtgccatcat gcatgaggtc agattcaatc accttggtca    6420
```

-continued

```
catcttcaca ttcactccac aaaacaatga gttccaactg cagctcagcc ccaagacttt   6480
tgcttcaaag acgtatggtc tgtgtgggat ctgtgatgag aacggagcca atgacttcat   6540
gctgagggat ggcacagtca ccacagactg gaaaacactt gttcaggaat ggactgtgca   6600
gcggccaggg cagacgtgcc agcccatcct ggaggagcag tgtcttgtcc ccgacagctc   6660
ccactgccag gtcctcctct taccactgtt tgctgaatgc cacaaggtcc tggctccagc   6720
cacattctat gccatctgcc agcaggacag ttgccaccag gagcaagtgt gtgaggtgat   6780
cgcctcttat gccccacctct gtcggaccaa cggggtctgc gttgactgga ggacacctga   6840
tttctgtgct atgtcatgcc caccatctct ggtctacaac cactgtgagc atggctgtcc   6900
ccggcactgt gatggcaacg tgagctcctg tggggaccat ccctccgaag gctgtttctg   6960
ccctccagat aaagtcatgt tggaaggcag ctgtgtccct gaagaggcct gcactcagtg   7020
cattggtgag gatggagtcc agcaccagtt cctggaagcc tgggtcccgg accaccagcc   7080
ctgtcagatc tgcacatgcc tcagcgggcg gaaggtcaac tgcacaacgc agccctgccc   7140
cacggccaaa gctcccacgt gtggcctgtg tgaagtagcc cgcctccgcc agaatgcaga   7200
ccagtgctgc cccgagtatg agtgtgtgtg tgacccagtg agctgtgacc tgcccccagt   7260
gcctcactgt gaacgtggcc tccagcccac actgaccaac cctggcgagt gcagacccaa   7320
cttcacctgc gcctgcagga aggaggagtg caaaagagtg tccccaccct cctgcccccc   7380
gcaccgtttg cccacccttc ggaagaccca gtgctgtgat gagtatgagt gtgcctgcaa   7440
ctgtgtcaac tccacagtga gctgtcccct tgggtacttg gcctcaactg ccaccaatga   7500
ctgtggctgt accacaacca cctgccttcc cgacaaggtg tgtgtccacc gaagcaccat   7560
ctaccctgtg ggccagttct gggaggaggg ctgcgatgtg tgcacctgca ccgacatgga   7620
ggatgccgtg atgggcctcc gcgtggccca gtgctcccag aagccctgtg aggacagctg   7680
tcggtcgggc ttcacttacg ttctgcatga aggcgagtgc tgtggaaggt gcctgccatc   7740
tgcctgtgag gtggtgactg gctcaccgcg gggggactcc cagtcttcct ggaagagtgt   7800
cggctcccag tgggcctccc cggagaaccc ctgcctcatc aatgagtgtg tccgagtgaa   7860
ggaggaggtc tttatacaac aaaggaacgt ctcctgcccc cagctggagg tccctgtctg   7920
cccctcgggc tttcagctga ctgtaagac ctcagcgtgc tgcccaagct gtcgctgtga   7980
gcgcatggag gcctgcatgc tcaatggcac tgtcattggg cccgggaaga ctgtgatgat   8040
cgatgtgtgc acgacctgcc gctgcatggt gcaggtgggg gtcatctctg gattcaagct   8100
ggagtgcagg aagaccacct gcaacccctg cccctggggt tacaaggaag aaaataacac   8160
aggtgaatgt tgtgggagat gtttgcctac ggcttgcacc attcagctaa gaggaggaca   8220
gatcatgaca ctgaagcgtg atgagacgct ccaggatggc tgtgatactc acttctgcaa   8280
ggtcaatgag agaggagagt acttctggga aagagggtc acaggctgcc caccctttga   8340
tgaacacaag tgtctggctg agggaggtaa aattatgaaa attccaggca cctgctgtga   8400
cacatgtgag gagcctgagt gcaacgacat cactgccagg ctgcagtatg tcaaggtggg   8460
aagctgtaag tctgaagtag aggtggatat ccactactgc caggggcaaat gtgccagcaa   8520 agccatgtac tccattgaca tcaacgatgt gcaggaccag tgctcctgct gctctccgac   8580
acggacggag cccatgcagg tggccctgca ctgcaccaat ggctctgttg tgtaccatga   8640
ggttctcaat gccatggagt gcaaatgctc ccccaggaag tgcagcaagt gaggctgctg   8700
```

```
cagctgcatg ggtgcctgct gctgcctgcc ttggcctgat ggccaggcca gagtgctgcc    8760
agtcctctgc atgttctgct cttgtgccct tctgagccca caataaaggc tgagctctta    8820
tcttgcaaaa ggc                                                       8833
```

```
<210> SEQ ID NO 2
<211> LENGTH: 2783
<212> TYPE: PRT
<213> ORGANISM: Homo sapiens

<400> SEQUENCE: 2

Met Ile Pro Ala Arg Phe Ala Gly Val Leu Leu Leu Ile Leu Pro Gly
1               5                   10                  15

Thr Leu Cys Ala Glu Gly Thr Arg Gly Arg Ser Ser Thr Ala Arg Cys
            20                  25                  30

Ser Leu Phe Gly Ser Asp Phe Val Asn Thr Phe Asp Gly Ser Met Tyr
        35                  40                  45

Ser Phe Ala Gly Tyr Cys Ser Tyr Leu Leu Ala Gly Gly Cys Gln Lys
    50                  55                  60

Arg Ser Phe Ser Ile Ile Gly Asp Phe Gln Asn Gly Lys Arg Val Ser
65                  70                  75                  80

Leu Ser Val Tyr Leu Gly Glu Phe Phe Asp Ile His Leu Phe Val Asn
                85                  90                  95

Gly Thr Val Thr Gln Gly Asp Gln Arg Val Ser Met Pro Tyr Ala Ser
            100                 105                 110

Lys Leu Glu Thr Glu Ala Gly Tyr Tyr Lys Leu Ser Gly Glu Ala Tyr
        115                 120                 125

Gly Phe Val Ala Arg Ile Asp Gly Ser Gly Asn Phe Gln Val Leu Leu
    130                 135                 140

Ser Asp Arg Tyr Phe Asn Lys Thr Cys Gly Leu Cys Gly Asn Phe Asn
145                 150                 155                 160

Ile Phe Ala Glu Asp Asp Phe Met Thr Gln Glu Gly Thr Leu Thr Ser
                165                 170                 175

Asp Pro Tyr Asp Phe Ala Asn Ser Trp Ala Leu Ser Ser Gly Glu Gln
            180                 185                 190

Trp Cys Glu Arg Pro Ser Ser Ser Cys Asn Ile Ser Ser Gly Glu Met
        195                 200                 205

Gln Lys Gly Leu Trp Glu Gln Cys Gln Leu Leu Lys Ser Thr Ser Val
    210                 215                 220

Phe Ala Arg Cys His Pro Leu Val Asp Pro Glu Pro Phe Cys Glu Lys
225                 230                 235                 240

Thr Leu Cys Glu Cys Ala Gly Gly Leu Glu Cys Ala Cys Pro Ala Leu
                245                 250                 255

Leu Glu Tyr Ala Arg Thr Cys Ala Gln Glu Gly Met Val Leu Tyr Gly
            260                 265                 270

Trp Thr Asp His Ser Ala Cys Ser Pro Val Cys Pro Ala Gly Met Glu
        275                 280                 285

Tyr Arg Gln Cys Val Ser Pro Cys Ala Arg Thr Cys Gln Ser Leu His
    290                 295                 300

Ile Asn Glu Met Cys Gln Glu Arg Cys Val Asp Gly Cys Ser Cys Pro
305                 310                 315                 320

Glu Gly Gln Leu Leu Asp Glu Gly Leu Cys Val Glu Ser Thr Glu Cys
                325                 330                 335
```

-continued

```
Pro Cys Val His Ser Gly Lys Arg Tyr Pro Pro Gly Thr Ser Leu Ser
        340                 345             350

Arg Asp Cys Asn Thr Cys Ile Cys Arg Asn Ser Gln Trp Ile Cys Ser
        355                 360             365

Asn Glu Glu Cys Pro Gly Glu Cys Leu Val Thr Gly Gln Ser His Phe
        370                 375             380

Lys Ser Phe Asp Asn Arg Tyr Phe Thr Phe Ser Gly Ile Cys Gln Tyr
385                 390                 395                 400

Leu Leu Ala Arg Asp Cys Gln Asp His Ser Phe Ser Ile Val Ile Glu
                405                 410                 415

Thr Val Gln Cys Ala Asp Asp Arg Asp Ala Val Cys Thr Arg Ser Val
        420                 425             430

Thr Val Arg Leu Pro Gly Leu His Asn Ser Leu Val Lys Leu Lys His
        435                 440             445

Gly Ala Gly Val Ala Met Asp Gly Gln Asp Val Gln Leu Pro Leu Leu
        450                 455             460

Lys Gly Asp Leu Arg Ile Gln His Thr Val Thr Ala Ser Val Arg Leu
465                 470                 475                 480

Ser Tyr Gly Glu Asp Leu Gln Met Asp Trp Asp Gly Arg Gly Arg Leu
                485                 490                 495

Leu Val Lys Leu Ser Pro Val Tyr Ala Gly Lys Thr Cys Gly Leu Cys
                500                 505                 510

Gly Asn Tyr Asn Gly Asn Gln Gly Asp Asp Phe Leu Thr Pro Ser Gly
                515                 520                 525

Leu Ala Glu Pro Arg Val Glu Asp Phe Gly Asn Ala Trp Lys Leu His
        530                 535                 540

Gly Asp Cys Gln Asp Leu Gln Lys Gln His Ser Asp Pro Cys Ala Leu
545                 550                 555                 560

Asn Pro Arg Met Thr Arg Phe Ser Glu Glu Ala Cys Ala Val Leu Thr
                565                 570                 575

Ser Pro Thr Phe Glu Ala Cys His Arg Ala Val Ser Pro Leu Pro Tyr
                580                 585                 590

Leu Arg Asn Cys Arg Tyr Asp Val Cys Ser Cys Ser Asp Gly Arg Glu
                595                 600                 605

Cys Leu Cys Gly Ser Tyr Ala Ala Ala Cys Ala Gly Arg Gly Val Arg
        610                 615                 620

Val Ala Trp Arg Glu Pro Gly Arg Cys Glu Leu Asn Cys Pro Lys Gly
625                 630                 635                 640

Gln Val Tyr Leu Gln Cys Gly Thr Pro Cys Asn Leu Thr Cys Arg Ser
                645                 650                 655

Leu Ser Tyr Pro Asp Glu Glu Cys Asn Glu Ala Cys Leu Glu Gly Cys
                660                 665                 670

Phe Cys Pro Pro Met Asp Glu Arg Gly Asp Cys Val Pro Lys Ala Gln
        675                 680                 685

Cys Pro Cys Tyr Tyr Asp Gly Glu Ile Phe Gln Pro Glu Asp Ile Phe
        690                 695                 700

Ser Asp His His Thr Met Cys Tyr Cys Glu Asp Gly Phe Met His Cys
705                 710                 715                 720

Thr Met Ser Gly Val Pro Gly Ser Leu Leu Pro Asp Ala Val Leu Ser
                725                 730                 735

Ser Pro Leu Ser His Arg Ser Lys Arg Ser Leu Ser Cys Arg Pro Pro
        740                 745                 750
```

```
Met Val Lys Leu Val Cys Pro Ala Asp Asn Leu Arg Ala Glu Gly Leu
        755                 760                 765

Glu Cys Thr Lys Thr Cys Gln Asn Tyr Asp Leu Glu Cys Met Ser Met
    770                 775                 780

Gly Cys Val Ser Gly Cys Leu Cys Pro Pro Gly Met Val Arg His Glu
785                 790                 795                 800

Asn Arg Cys Glu Arg Cys Pro Cys Phe His Gln Gly Lys Glu Tyr Ala
                805                 810                 815

Pro Gly Glu Thr Val Lys Ile Gly Cys Asn Thr Cys Val Cys Arg Asp
            820                 825                 830

Arg Lys Trp Asn Cys Thr Asp His Val Cys Asp Ala Thr Cys Ser Thr
        835                 840                 845

Ile Gly Met Ala His Tyr Leu Thr Phe Asp Gly Leu Lys Tyr Leu Phe
    850                 855                 860

Pro Gly Glu Cys Gln Tyr Val Leu Val Gln Asp Tyr Cys Gly Ser Asn
865                 870                 875                 880

Pro Gly Thr Phe Arg Ile Leu Val Gly Asn Lys Gly Cys Ser His Pro
                885                 890                 895

Ser Val Lys Cys Lys Lys Arg Val Thr Ile Leu Val Glu Gly Gly Glu
            900                 905                 910

Ile Glu Leu Phe Asp Gly Glu Val Asn Val Lys Arg Pro Met Lys Asp
    915                 920                 925

Glu Thr His Phe Glu Val Val Glu Ser Gly Arg Tyr Ile Ile Leu Leu
    930                 935                 940

Leu Gly Lys Ala Leu Ser Val Val Trp Asp Arg His Leu Ser Ile Ser
945                 950                 955                 960

Val Val Leu Lys Gln Thr Tyr Gln Glu Lys Val Cys Gly Leu Cys Gly
                965                 970                 975

Asn Phe Asp Gly Ile Gln Asn Asn Asp Leu Thr Ser Ser Asn Leu Gln
                980                 985                 990

Val Glu Glu Asp Pro Val Asp Phe  Gly Asn Ser Trp Lys  Val Ser Ser
        995                 1000                1005

Gln Cys  Ala Asp Thr Arg Lys  Val Pro Leu Asp Ser  Ser Pro Ala
    1010                1015                1020

Thr Cys  His Asn Asn Ile Met  Lys Gln Thr Met Val  Asp Ser Ser
    1025                1030                1035

Cys Arg  Ile Leu Thr Ser Asp  Val Phe Gln Asp Cys  Asn Lys Leu
    1040                1045                1050

Val Asp  Pro Glu Pro Tyr Leu  Asp Val Cys Ile Tyr  Asp Thr Cys
    1055                1060                1065

Ser Cys  Glu Ser Ile Gly Asp  Cys Ala Cys Phe Cys  Asp Thr Ile
    1070                1075                1080

Ala Ala  Tyr Ala His Val Cys  Ala Gln His Gly Lys  Val Val Thr
    1085                1090                1095

Trp Arg  Thr Ala Thr Leu Cys  Pro Gln Ser Cys Glu  Glu Arg Asn
    1100                1105                1110

Leu Arg  Glu Asn Gly Tyr Glu  Cys Glu Trp Arg Tyr  Asn Ser Cys
    1115                1120                1125

Ala Pro  Ala Cys Gln Val Thr  Cys Gln His Pro Glu  Pro Leu Ala
    1130                1135                1140

Cys Pro  Val Gln Cys Val Glu  Gly Cys His Ala His  Cys Pro Pro
    1145                1150                1155
```

-continued

```
Gly Lys  Ile Leu Asp Glu Leu  Leu Gln Thr Cys Val  Asp Pro Glu
    1160             1165             1170

Asp Cys  Pro Val Cys Glu Val  Ala Gly Arg Arg Phe  Ala Ser Gly
    1175             1180             1185

Lys Lys  Val Thr Leu Asn Pro  Ser Asp Pro Glu His  Cys Gln Ile
    1190             1195             1200

Cys His  Cys Asp Val Val Asn  Leu Thr Cys Glu Ala  Cys Gln Glu
    1205             1210             1215

Pro Gly  Gly Leu Val Val Pro  Pro Thr Asp Ala Pro  Val Ser Pro
    1220             1225             1230

Thr Thr  Leu Tyr Val Glu Asp  Ile Ser Glu Pro Pro  Leu His Asp
    1235             1240             1245

Phe Tyr  Cys Ser Arg Leu Leu  Asp Leu Val Phe Leu  Leu Asp Gly
    1250             1255             1260

Ser Ser  Arg Leu Ser Glu Ala  Glu Phe Glu Val Leu  Lys Ala Phe
    1265             1270             1275

Val Val  Asp Met Met Glu Arg  Leu Arg Ile Ser Gln  Lys Trp Val
    1280             1285             1290

Arg Val  Ala Val Val Glu Tyr  His Asp Gly Ser His  Ala Tyr Ile
    1295             1300             1305

Gly Leu  Lys Asp Arg Lys Arg  Pro Ser Glu Leu Arg  Arg Ile Ala
    1310             1315             1320

Ser Gln  Val Lys Tyr Ala Gly  Ser Gln Val Ala Ser  Thr Ser Glu
    1325             1330             1335

Val Leu  Lys Tyr Thr Leu Phe  Gln Ile Phe Ser Lys  Ile Asp Arg
    1340             1345             1350

Pro Glu  Ala Ser Arg Ile Thr  Leu Leu Leu Met Ala  Ser Gln Glu
    1355             1360             1365

Pro Gln  Arg Met Ser Arg Asn  Phe Val Arg Tyr Val  Gln Gly Leu
    1370             1375             1380

Lys Lys  Lys Lys Val Ile Val  Ile Pro Val Gly Ile  Gly Pro His
    1385             1390             1395

Ala Asn  Leu Lys Gln Ile Arg  Leu Ile Glu Lys Gln  Ala Pro Glu
    1400             1405             1410

Asn Lys  Ala Phe Val Leu Ser  Ser Val Asp Glu Leu  Glu Gln Gln
    1415             1420             1425

Arg Asp  Glu Ile Val Ser Tyr  Leu Cys Asp Leu Ala  Pro Glu Ala
    1430             1435             1440

Pro Pro  Pro Thr Leu Pro Pro  Asp Met Ala Gln Val  Thr Val Gly
    1445             1450             1455

Pro Gly  Leu Leu Gly Val Ser  Thr Leu Gly Pro Lys  Arg Asn Ser
    1460             1465             1470

Met Val  Leu Asp Val Ala Phe  Val Leu Glu Gly Ser  Asp Lys Ile
    1475             1480             1485

Gly Glu  Ala Asp Phe Asn Arg  Ser Lys Glu Phe Met  Glu Glu Val
    1490             1495             1500

Ile Gln  Arg Met Asp Val Gly  Gln Asp Ser Ile His  Val Thr Val
    1505             1510             1515

Leu Gln  Tyr Ser Tyr Met Val  Thr Val Glu Tyr Pro  Phe Ser Glu
    1520             1525             1530

Ala Gln  Ser Lys Gly Asp Ile  Leu Gln Arg Val Arg  Glu Ile Arg
    1535             1540             1545
```

```
Tyr Gln Gly Gly Asn Arg Thr Asn Thr Gly Leu Ala Leu Arg Tyr
    1550            1555            1560

Leu Ser Asp His Ser Phe Leu Val Ser Gln Gly Asp Arg Glu Gln
    1565            1570            1575

Ala Pro Asn Leu Val Tyr Met Val Thr Gly Asn Pro Ala Ser Asp
    1580            1585            1590

Glu Ile Lys Arg Leu Pro Gly Asp Ile Gln Val Val Pro Ile Gly
    1595            1600            1605

Val Gly Pro Asn Ala Asn Val Gln Glu Leu Glu Arg Ile Gly Trp
    1610            1615            1620

Pro Asn Ala Pro Ile Leu Ile Gln Asp Phe Glu Thr Leu Pro Arg
    1625            1630            1635

Glu Ala Pro Asp Leu Val Leu Gln Arg Cys Cys Ser Gly Glu Gly
    1640            1645            1650

Leu Gln Ile Pro Thr Leu Ser Pro Ala Pro Asp Cys Ser Gln Pro
    1655            1660            1665

Leu Asp Val Ile Leu Leu Leu Asp Gly Ser Ser Ser Phe Pro Ala
    1670            1675            1680

Ser Tyr Phe Asp Glu Met Lys Ser Phe Ala Lys Ala Phe Ile Ser
    1685            1690            1695

Lys Ala Asn Ile Gly Pro Arg Leu Thr Gln Val Ser Val Leu Gln
    1700            1705            1710

Tyr Gly Ser Ile Thr Thr Ile Asp Val Pro Trp Asn Val Val Pro
    1715            1720            1725

Glu Lys Ala His Leu Leu Ser Leu Val Asp Val Met Gln Arg Glu
    1730            1735            1740

Gly Gly Pro Ser Gln Ile Gly Asp Ala Leu Gly Phe Ala Val Arg
    1745            1750            1755

Tyr Leu Thr Ser Glu Met His Gly Ala Arg Pro Gly Ala Ser Lys
    1760            1765            1770

Ala Val Val Ile Leu Val Thr Asp Val Ser Val Asp Ser Val Asp
    1775            1780            1785

Ala Ala Ala Asp Ala Ala Arg Ser Asn Arg Val Thr Val Phe Pro
    1790            1795            1800

Ile Gly Ile Gly Asp Arg Tyr Asp Ala Ala Gln Leu Arg Ile Leu
    1805            1810            1815

Ala Gly Pro Ala Gly Asp Ser Asn Val Val Lys Leu Gln Arg Ile
    1820            1825            1830

Glu Asp Leu Pro Thr Met Val Thr Leu Gly Asn Ser Phe Leu His
    1835            1840            1845

Lys Leu Cys Ser Gly Phe Val Arg Ile Cys Met Asp Glu Asp Gly
    1850            1855            1860

Asn Glu Lys Arg Pro Gly Asp Val Trp Thr Leu Pro Asp Gln Cys
    1865            1870            1875

His Thr Val Thr Cys Gln Pro Asp Gly Gln Thr Leu Leu Lys Ser
    1880            1885            1890

His Arg Val Asn Cys Asp Arg Gly Leu Arg Pro Ser Cys Pro Asn
    1895            1900            1905

Ser Gln Ser Pro Val Lys Val Glu Glu Thr Cys Gly Cys Arg Trp
    1910            1915            1920

Thr Cys Pro Cys Val Cys Thr Gly Ser Ser Thr Arg His Ile Val
    1925            1930            1935
```

-continued

```
Thr Phe Asp Gly Gln Asn Phe  Lys Leu Thr Gly Ser  Cys Ser Tyr
    1940              1945              1950

Val Leu Phe Gln Asn Lys Glu  Gln Asp Leu Glu Val  Ile Leu His
    1955              1960              1965

Asn Gly Ala Cys Ser Pro Gly  Ala Arg Gln Gly Cys  Met Lys Ser
    1970              1975              1980

Ile Glu Val Lys His Ser Ala  Leu Ser Val Glu Leu  His Ser Asp
    1985              1990              1995

Met Glu Val Thr Val Asn Gly  Arg Leu Val Ser Val  Pro Tyr Val
    2000              2005              2010

Gly Gly Asn Met Glu Val Asn  Val Tyr Gly Ala Ile  Met His Glu
    2015              2020              2025

Val Arg Phe Asn His Leu Gly  His Ile Phe Thr Phe  Thr Pro Gln
    2030              2035              2040

Asn Asn Glu Phe Gln Leu Gln  Leu Ser Pro Lys Thr  Phe Ala Ser
    2045              2050              2055

Lys Thr Tyr Gly Leu Cys Gly  Ile Cys Asp Glu Asn  Gly Ala Asn
    2060              2065              2070

Asp Phe Met Leu Arg Asp Gly  Thr Val Thr Thr Asp  Trp Lys Thr
    2075              2080              2085

Leu Val Gln Glu Trp Thr Val  Gln Arg Pro Gly Gln  Thr Cys Gln
    2090              2095              2100

Pro Glu Gln Cys Leu Val Pro  Asp Ser Ser His Cys  Gln Val Leu
    2105              2110              2115

Leu Leu Pro Leu Phe Ala Glu  Cys His Lys Val Leu  Ala Pro Ala
    2120              2125              2130

Thr Phe Tyr Ala Ile Cys Gln  Gln Asp Ser Cys His  Gln Glu Gln
    2135              2140              2145

Val Cys Glu Val Ile Ala Ser  Tyr Ala His Leu Cys  Arg Thr Asn
    2150              2155              2160

Gly Val Cys Val Asp Trp Arg  Thr Pro Asp Phe Cys  Ala Met Ser
    2165              2170              2175

Cys Pro Pro Ser Leu Val Tyr  Asn His Cys Glu His  Gly Cys Pro
    2180              2185              2190

Arg His Cys Asp Gly Asn Val  Ser Ser Cys Gly Asp  His Pro Ser
    2195              2200              2205

Glu Gly Cys Phe Cys Pro Pro  Asp Lys Val Met Leu  Glu Gly Ser
    2210              2215              2220

Cys Val Pro Glu Glu Ala Cys  Thr Gln Cys Ile Gly  Glu Asp Gly
    2225              2230              2235

Val Gln His Gln Phe Leu Glu  Ala Trp Val Pro Asp  His Gln Pro
    2240              2245              2250

Cys Gln Ile Cys Thr Cys Leu  Ser Gly Arg Lys Val  Asn Cys Thr
    2255              2260              2265

Thr Gln Pro Cys Pro Thr Ala  Lys Ala Pro Thr Cys  Gly Leu Cys
    2270              2275              2280

Glu Val Ala Arg Leu Arg Gln  Asn Ala Asp Gln Cys  Cys Pro Glu
    2285              2290              2295

Tyr Glu Cys Val Cys Asp Pro  Val Ser Cys Asp Leu  Pro Pro Val
    2300              2305              2310

Pro His Cys Glu Arg Gly Leu  Gln Pro Thr Leu Thr  Asn Pro Gly
    2315              2320              2325
```

-continued

```
Glu Cys Arg Pro Asn Phe Thr  Cys Ala Cys Arg Lys  Glu Glu Cys
2330                2335                2340

Lys Arg Val Ser Pro Pro Ser  Cys Pro Pro His Arg  Leu Pro Thr
2345                2350                2355

Leu Arg Lys Thr Gln Cys Cys  Asp Glu Tyr Glu Cys  Ala Cys Asn
2360                2365                2370

Cys Val Asn Ser Thr Val Ser  Cys Pro Leu Gly Tyr  Leu Ala Ser
2375                2380                2385

Thr Ala Thr Asn Asp Cys Gly  Cys Thr Thr Thr  Cys Leu Pro
2390                2395                2400

Asp Lys Val Cys Val His Arg  Ser Thr Ile Tyr Pro  Val Gly Gln
2405                2410                2415

Phe Trp Glu Glu Gly Cys Asp  Val Cys Thr Cys Thr  Asp Met Glu
2420                2425                2430

Asp Ala Val Met Gly Leu Arg  Val Ala Gln Cys Ser  Gln Lys Pro
2435                2440                2445

Cys Glu Asp Ser Cys Arg Ser  Gly Phe Thr Tyr Val  Leu His Glu
2450                2455                2460

Gly Glu Cys Cys Gly Arg Cys  Leu Pro Ser Ala Cys  Glu Val Val
2465                2470                2475

Thr Gly Ser Pro Arg Gly Asp  Ser Gln Ser Ser Trp  Lys Ser Val
2480                2485                2490

Gly Ser Gln Trp Glu Asn Pro  Cys Leu Ile Asn Glu  Cys Val Arg
2495                2500                2505

Val Lys Glu Glu Val Phe Ile  Gln Gln Arg Asn Val  Ser Cys Pro
2510                2515                2520

Gln Leu Glu Val Pro Val Cys  Pro Ser Gly Phe Gln  Leu Ser Cys
2525                2530                2535

Lys Thr Ser Ala Cys Cys Pro  Ser Cys Arg Cys Glu  Arg Met Glu
2540                2545                2550

Ala Cys Met Leu Asn Gly Thr  Val Ile Gly Pro Gly  Lys Thr Val
2555                2560                2565

Met Ile Asp Val Cys Thr Thr  Cys Arg Cys Met Val  Gln Val Gly
2570                2575                2580

Val Ile Ser Gly Phe Lys Leu  Glu Cys Arg Lys Thr  Thr Cys Asn
2585                2590                2595

Pro Cys Pro Leu Gly Tyr Lys  Glu Glu Asn Asn Thr  Gly Glu Cys
2600                2605                2610

Cys Gly Arg Cys Leu Pro Thr  Ala Cys Thr Ile Gln  Leu Arg Gly
2615                2620                2625

Gly Gln Ile Met Thr Leu Lys  Arg Asp Glu Thr Leu  Gln Asp Gly
2630                2635                2640

Cys Asp Thr His Phe Cys Lys  Val Asn Glu Arg Gly  Glu Tyr Phe
2645                2650                2655

Trp Glu Lys Arg Val Thr Gly  Cys Pro Pro Phe Asp  Glu His Lys
2660                2665                2670

Cys Leu Ala Glu Gly Gly Lys  Ile Met Lys Ile Pro  Gly Thr Cys
2675                2680                2685

Cys Asp Thr Cys Glu Glu Pro  Glu Cys Asn Asp Ile  Thr Ala Arg
2690                2695                2700

Leu Gln Tyr Val Lys Val Gly  Ser Cys Lys Ser Glu  Val Glu Val
2705                2710                2715
```

-continued

```
Asp Ile  His Tyr Cys Gln Gly  Lys Cys Ala Ser Lys  Ala Met Tyr
    2720             2725             2730

Ser Ile  Asp Ile Asn Asp Val  Gln Asp Gln Cys Ser  Cys Cys Ser
    2735             2740             2745

Pro Thr  Arg Thr Glu Pro Met  Gln His Cys Thr Asn  Gly Ser Val
    2750             2755             2760

Val Tyr  His Glu Val Leu Asn  Ala Met Glu Cys Lys  Cys Ser Pro
    2765             2770             2775

Arg Lys  Cys Ser Lys
    2780

<210> SEQ ID NO 3
<211> LENGTH: 2050
<212> TYPE: PRT
<213> ORGANISM: Homo sapiens

<400> SEQUENCE: 3

Ser Leu Ser Cys Arg Pro Pro Met Val Lys Leu Val Cys Pro Ala Asp
1               5               10              15

Asn Leu Arg Ala Glu Gly Leu Glu Cys Thr Lys Thr Cys Gln Asn Tyr
            20              25              30

Asp Leu Glu Cys Met Ser Met Gly Cys Val Ser Gly Cys Leu Cys Pro
        35              40              45

Pro Gly Met Val Arg His Glu Asn Arg Cys Val Ala Leu Glu Arg Cys
        50              55              60

Pro Cys Phe His Gln Gly Lys Glu Tyr Ala Pro Gly Glu Thr Val Lys
65              70              75                      80

Ile Gly Cys Asn Thr Cys Val Cys Arg Asp Arg Lys Trp Asn Cys Thr
                85              90              95

Asp His Val Cys Asp Ala Thr Cys Ser Thr Ile Gly Met Ala His Tyr
            100             105             110

Leu Thr Phe Asp Gly Leu Lys Tyr Leu Phe Pro Gly Glu Cys Gln Tyr
        115             120             125

Val Leu Val Gln Asp Tyr Cys Gly Ser Asn Pro Gly Thr Phe Arg Ile
    130             135             140

Leu Val Gly Asn Lys Gly Cys Ser His Pro Ser Val Lys Cys Lys Lys
145             150             155             160

Arg Val Thr Ile Leu Val Glu Gly Gly Glu Ile Glu Leu Phe Asp Gly
            165             170             175

Glu Val Asn Val Lys Arg Pro Met Lys Asp Glu Thr His Phe Glu Val
            180             185             190

Val Glu Ser Gly Arg Tyr Ile Ile Leu Leu Leu Gly Lys Ala Leu Ser
        195             200             205

Val Val Trp Asp Arg His Leu Ser Ile Ser Val Val Leu Lys Gln Thr
    210             215             220

Tyr Gln Glu Lys Val Cys Gly Leu Cys Gly Asn Phe Asp Gly Ile Gln
225             230             235             240

Asn Asn Asp Leu Thr Ser Ser Asn Leu Gln Val Glu Glu Asp Pro Val
            245             250             255

Asp Phe Gly Asn Ser Trp Lys Val Ser Ser Gln Cys Ala Asp Thr Arg
            260             265             270

Lys Val Pro Leu Asp Ser Ser Pro Ala Thr Cys His Asn Asn Ile Met
    275             280             285
```

-continued

```
Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
                435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
                500                 505                 510

Leu Asp Leu Val Phe Leu Leu Asp Gly Ser Ser Arg Leu Ser Glu Ala
                515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
                580                 585                 590

Ser Thr Ser Glu Val Leu Lys Tyr Thr Leu Phe Gln Ile Phe Ser Lys
                595                 600                 605

Ile Asp Arg Pro Glu Ala Ser Arg Ile Thr Leu Leu Leu Met Ala Ser
    610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
                660                 665                 670

Lys Ala Phe Val Leu Ser Ser Val Asp Glu Leu Glu Gln Gln Arg Asp
                675                 680                 685

Glu Ile Val Ser Tyr Leu Cys Asp Leu Ala Pro Glu Ala Pro Pro Pro
    690                 695                 700
```

-continued

```
Thr Leu Pro Pro Asp Met Ala Gln Val Thr Val Gly Pro Gly Leu Leu
705             710             715             720

Gly Val Ser Thr Leu Gly Pro Lys Arg Asn Ser Met Val Leu Asp Val
            725             730             735

Ala Phe Val Leu Glu Gly Ser Asp Lys Ile Gly Glu Ala Asp Phe Asn
            740             745             750

Arg Ser Lys Glu Phe Met Glu Glu Val Ile Gln Arg Met Asp Val Gly
            755             760             765

Gln Asp Ser Ile His Val Thr Val Leu Gln Tyr Ser Tyr Met Val Thr
    770             775             780

Val Glu Tyr Pro Phe Ser Glu Ala Gln Ser Lys Gly Asp Ile Leu Gln
785             790             795             800

Arg Val Arg Glu Ile Arg Tyr Gln Gly Gly Asn Arg Thr Asn Thr Gly
            805             810             815

Leu Ala Leu Arg Tyr Leu Ser Asp His Ser Phe Leu Val Ser Gln Gly
            820             825             830

Asp Arg Glu Gln Ala Pro Asn Leu Val Tyr Met Val Thr Gly Asn Pro
            835             840             845

Ala Ser Asp Glu Ile Lys Arg Leu Pro Gly Asp Ile Gln Val Val Pro
850             855             860

Ile Gly Val Gly Pro Asn Ala Asn Val Gln Glu Leu Glu Arg Ile Gly
865             870             875             880

Trp Pro Asn Ala Pro Ile Leu Ile Gln Asp Phe Glu Thr Leu Pro Arg
            885             890             895

Glu Ala Pro Asp Leu Val Leu Gln Arg Cys Cys Ser Gly Glu Gly Leu
            900             905             910

Gln Ile Pro Thr Leu Ser Pro Ala Pro Asp Cys Ser Gln Pro Leu Asp
            915             920             925

Val Ile Leu Leu Leu Asp Gly Ser Ser Ser Phe Pro Ala Ser Tyr Phe
    930             935             940

Asp Glu Met Lys Ser Phe Ala Lys Ala Phe Ile Ser Lys Ala Asn Ile
945             950             955             960

Gly Pro Arg Leu Thr Gln Val Ser Val Leu Gln Tyr Gly Ser Ile Thr
            965             970             975

Thr Ile Asp Val Pro Trp Asn Val Val Pro Glu Lys Ala His Leu Leu
            980             985             990

Ser Leu Val Asp Val Met Gln Arg Glu Gly Gly Pro Ser Gln Ile Gly
    995             1000                1005

Asp Ala Leu Gly Phe Ala Val Arg Tyr Leu Thr Ser Glu Met His
    1010            1015               1020

Gly Ala Arg Pro Gly Ala Ser Lys Ala Val Val Ile Leu Val Thr
    1025            1030               1035

Asp Val Ser Val Asp Ser Val Asp Ala Ala Ala Asp Ala Ala Arg
    1040            1045               1050

Ser Asn Arg Val Thr Val Phe Pro Ile Gly Ile Gly Asp Arg Tyr
    1055            1060               1065

Asp Ala Ala Gln Leu Arg Ile Leu Ala Gly Pro Ala Gly Asp Ser
    1070            1075               1080

Asn Val Val Lys Leu Gln Arg Ile Glu Asp Leu Pro Thr Met Val
    1085            1090               1095

Thr Leu Gly Asn Ser Phe Leu His Lys Leu Cys Ser Gly Phe Val
    1100            1105               1110
```

```
Arg Ile Cys Met Asp Glu Asp Gly Asn Glu Lys Arg Pro Gly Asp
    1115                1120                1125

Val Trp Thr Leu Pro Asp Gln Cys His Thr Val Thr Cys Gln Pro
    1130                1135                1140

Asp Gly Gln Thr Leu Leu Lys Ser His Arg Val Asn Cys Asp Arg
    1145                1150                1155

Gly Leu Arg Pro Ser Cys Pro Asn Ser Gln Ser Pro Val Lys Val
    1160                1165                1170

Glu Glu Thr Cys Gly Cys Arg Trp Thr Cys Pro Cys Val Cys Thr
    1175                1180                1185

Gly Ser Ser Thr Arg His Ile Val Thr Phe Asp Gly Gln Asn Phe
    1190                1195                1200

Lys Leu Thr Gly Ser Cys Ser Tyr Val Leu Phe Gln Asn Lys Glu
    1205                1210                1215

Gln Asp Leu Glu Val Ile Leu His Asn Gly Ala Cys Ser Pro Gly
    1220                1225                1230

Ala Arg Gln Gly Cys Met Lys Ser Ile Glu Val Lys His Ser Ala
    1235                1240                1245

Leu Ser Val Glu Leu His Ser Asp Met Glu Val Thr Val Asn Gly
    1250                1255                1260

Arg Leu Val Ser Val Pro Tyr Val Gly Gly Asn Met Glu Val Asn
    1265                1270                1275

Val Tyr Gly Ala Ile Met His Glu Val Arg Phe Asn His Leu Gly
    1280                1285                1290

His Ile Phe Thr Phe Thr Pro Gln Asn Asn Glu Phe Gln Leu Gln
    1295                1300                1305

Leu Ser Pro Lys Thr Phe Ala Ser Lys Thr Tyr Gly Leu Cys Gly
    1310                1315                1320

Ile Cys Asp Glu Asn Gly Ala Asn Asp Phe Met Leu Arg Asp Gly
    1325                1330                1335

Thr Val Thr Thr Asp Trp Lys Thr Leu Val Gln Glu Trp Thr Val
    1340                1345                1350

Gln Arg Pro Gly Gln Thr Cys Gln Pro Ile Leu Glu Glu Gln Cys
    1355                1360                1365

Leu Val Pro Asp Ser Ser His Cys Gln Val Leu Leu Leu Pro Leu
    1370                1375                1380

Phe Ala Glu Cys His Lys Val Leu Ala Pro Ala Thr Phe Tyr Ala
    1385                1390                1395

Ile Cys Gln Gln Asp Ser Cys His Gln Glu Gln Val Cys Glu Val
    1400                1405                1410

Ile Ala Ser Tyr Ala His Leu Cys Arg Thr Asn Gly Val Cys Val
    1415                1420                1425

Asp Trp Arg Thr Pro Asp Phe Cys Ala Met Ser Cys Pro Pro Ser
    1430                1435                1440

Leu Val Tyr Asn His Cys Glu His Gly Cys Pro Arg His Cys Asp
    1445                1450                1455

Gly Asn Val Ser Ser Cys Gly Asp His Pro Ser Glu Gly Cys Phe
    1460                1465                1470

Cys Pro Pro Asp Lys Val Met Leu Glu Gly Ser Cys Val Pro Glu
    1475                1480                1485

Glu Ala Cys Thr Gln Cys Ile Gly Glu Asp Gly Val Gln His Gln
    1490                1495                1500
```

-continued

```
Phe Leu Glu Ala Trp Val Pro Asp His Gln Pro Cys Gln Ile Cys
    1505            1510            1515

Thr Cys Leu Ser Gly Arg Lys Val Asn Cys Thr Thr Gln Pro Cys
    1520            1525            1530

Pro Thr Ala Lys Ala Pro Thr Cys Gly Leu Cys Glu Val Ala Arg
    1535            1540            1545

Leu Arg Gln Asn Ala Asp Gln Cys Cys Pro Glu Tyr Glu Cys Val
    1550            1555            1560

Cys Asp Pro Val Ser Cys Asp Leu Pro Pro Val Pro His Cys Glu
    1565            1570            1575

Arg Gly Leu Gln Pro Thr Leu Thr Asn Pro Gly Glu Cys Arg Pro
    1580            1585            1590

Asn Phe Thr Cys Ala Cys Arg Lys Glu Glu Cys Lys Arg Val Ser
    1595            1600            1605

Pro Pro Ser Cys Pro Pro His Arg Leu Pro Thr Leu Arg Lys Thr
    1610            1615            1620

Gln Cys Cys Asp Glu Tyr Glu Cys Ala Cys Asn Cys Val Asn Ser
    1625            1630            1635

Thr Val Ser Cys Pro Leu Gly Tyr Leu Ala Ser Thr Ala Thr Asn
    1640            1645            1650

Asp Cys Gly Cys Thr Thr Thr Thr Cys Leu Pro Asp Lys Val Cys
    1655            1660            1665

Val His Arg Ser Thr Ile Tyr Pro Val Gly Gln Phe Trp Glu Glu
    1670            1675            1680

Gly Cys Asp Val Cys Thr Cys Thr Asp Met Glu Asp Ala Val Met
    1685            1690            1695

Gly Leu Arg Val Ala Gln Cys Ser Gln Lys Pro Cys Glu Asp Ser
    1700            1705            1710

Cys Arg Ser Gly Phe Thr Tyr Val Leu His Glu Gly Glu Cys Cys
    1715            1720            1725

Gly Arg Cys Leu Pro Ser Ala Cys Glu Val Val Thr Gly Ser Pro
    1730            1735            1740

Arg Gly Asp Ser Gln Ser Ser Trp Lys Ser Val Gly Ser Gln Trp
    1745            1750            1755

Ala Ser Pro Glu Asn Pro Cys Leu Ile Asn Glu Cys Val Arg Val
    1760            1765            1770

Lys Glu Glu Val Phe Ile Gln Gln Arg Asn Val Ser Cys Pro Gln
    1775            1780            1785

Leu Glu Val Pro Val Cys Pro Ser Gly Phe Gln Leu Ser Cys Lys
    1790            1795            1800

Thr Ser Ala Cys Cys Pro Ser Cys Arg Cys Glu Arg Met Glu Ala
    1805            1810            1815

Cys Met Leu Asn Gly Thr Val Ile Gly Pro Gly Lys Thr Val Met
    1820            1825            1830

Ile Asp Val Cys Thr Thr Cys Arg Cys Met Val Gln Val Gly Val
    1835            1840            1845

Ile Ser Gly Phe Lys Leu Glu Cys Arg Lys Thr Thr Cys Asn Pro
    1850            1855            1860

Cys Pro Leu Gly Tyr Lys Glu Glu Asn Asn Thr Gly Glu Cys Cys
    1865            1870            1875

Gly Arg Cys Leu Pro Thr Ala Cys Thr Ile Gln Leu Arg Gly Gly
    1880            1885            1890
```

-continued

```
Gln Ile Met Thr Leu Lys Arg Asp Glu Thr Leu Gln Asp Gly Cys
    1895                1900              1905

Asp Thr His Phe Cys Lys Val Asn Glu Arg Gly Glu Tyr Phe Trp
    1910                1915              1920

Glu Lys Arg Val Thr Gly Cys Pro Pro Phe Asp Glu His Lys Cys
    1925                1930              1935

Leu Ala Glu Gly Gly Lys Ile Met Lys Ile Pro Gly Thr Cys Cys
    1940                1945              1950

Asp Thr Cys Glu Glu Pro Glu Cys Asn Asp Ile Thr Ala Arg Leu
    1955                1960              1965

Gln Tyr Val Lys Val Gly Ser Cys Lys Ser Glu Val Glu Val Asp
    1970                1975              1980

Ile His Tyr Cys Gln Gly Lys Cys Ala Ser Lys Ala Met Tyr Ser
    1985                1990              1995

Ile Asp Ile Asn Asp Val Gln Asp Gln Cys Ser Cys Cys Ser Pro
    2000                2005              2010

Thr Arg Thr Glu Pro Met Gln Val Ala Leu His Cys Thr Asn Gly
    2015                2020              2025

Ser Val Val Tyr His Glu Val Leu Asn Ala Met Glu Cys Lys Cys
    2030                2035              2040

Ser Pro Arg Lys Cys Ser Lys
    2045                2050
```

LYOPHILIZED RECOMBINANT VWF FORMULATIONS

PRIORITY

This application is a divisional of U.S. patent application Ser. No. 16/258,488, filed Jan. 25, 2019, now U.S. Pat. No. 11,197,916, and is also a divisional of Ser. No. 16/258,490, filed Jan. 25, 2019, now U.S. Pat. No. 11,191,813, which are both divisionals of U.S. patent application Ser. No. 14/939, 364, filed Nov. 12, 2015, now U.S. Pat. No. 10,232,022, which is a continuation of U.S. patent application Ser. No. 12/603,064, filed Oct. 21, 2009, now abandoned, which claims priority to U.S. Provisional Application No. 61/107, 273, filed Oct. 21, 2008, and U.S. patent application Ser. Nos. 16/258,488 and 16/258,490 are also both continuations of U.S. patent application Ser. No. 14/693,078, filed Apr. 22, 2015, now U.S. Pat. No. 11,191,837, which is a continuation of U.S. patent application Ser. No. 12/342,646, filed Dec. 23, 2008, now abandoned, which claims priority to U.S. Provisional Application No. 61/017,881, filed Dec. 31, 2007, and which claims priority to U.S. Provisional Application No. 61/017,418 filed Dec. 28, 2007.

SEQUENCE LISTING

The instant application contains a Sequence Listing which has been submitted electronically in ASCII format and is hereby incorporated by reference in its entirety. Said ASCII copy, created on Oct. 22, 2021, is named 008073-5131-US05.txt and is 54,683 bytes in size.

FIELD OF THE INVENTION

Generally, the invention relates to formulations of lyophilized recombinant VWF and methods for making a lyophilized composition comprising recombinant VWF.

BACKGROUND OF THE INVENTION

Von Willebrand factor (VWF) is a glycoprotein circulating in plasma as a series of multimers ranging in size from about 500 to 20,000 kD. Multimeric forms of VWF are composed of 250 kD polypeptide subunits linked together by disulfide bonds. VWF mediates initial platelet adhesion to the sub-endothelium of the damaged vessel wall. Only the larger multimers exhibit hemostatic activity. It is assumed that endothelial cells secrete large polymeric forms of VWF and those forms of VWF which have a low molecular weight (low molecular weight VWF) arise from proteolytic cleavage. The multimers having large molecular masses are stored in the Weibel-Pallade bodies of endothelial cells and liberated upon stimulation.

VWF is synthesized by endothelial cells and megakaryocytes as prepro-VWF that consists to a large extent of repeated domains. Upon cleavage of the signal peptide, pro-VWF dimerizes through disulfide linkages at its C-terminal region. The dimers serve as protomers for multimerization, which is governed by disulfide linkages between the free end termini. The assembly to multimers is followed by the proteolytic removal of the propeptide sequence (Leyte et al., Biochem. J. 274 (1991), 257-261).

The primary translation product predicted from the cloned cDNA of VWF is a 2813-residue precursor polypeptide (prepro-VWF). The prepro-VWF consists of a 22 amino acid signal peptide and a 741 amino acid propeptide, with the mature VWF comprising 2050 amino acids (Ruggeri Z. A., and Ware, J., FASEB J., 308-316 (1993)).

Defects in VWF are causal to Von Willebrand disease (VWD), which is characterized by a more or less pronounced bleeding phenotype. VWD type 3 is the most severe form in which VWF is completely missing, and VWD type 1 relates to a quantitative loss of VWF and its phenotype can be very mild. VWD type 2 relates to qualitative defects of VWF and can be as severe as VWD type 3. VWD type 2 has many sub forms, some being associated with the loss or the decrease of high molecular weight multimers. Von Willebrand syndrome type 2a (VWS-2A) is characterized by a loss of both intermediate and large multimers. VWS-2B is characterized by a loss of highest-molecular-weight multimers. Other diseases and disorders related to VWF are known in the art.

U.S. Pat. Nos. 6,531,577, 7,166,709, and European Patent Application No. 04380188.5, describe plasma-derived VWF formulations. However, in addition to quantity and purity issues with plasma-derived VWF, there is also a risk of blood-born pathogens (e.g., viruses and Variant Creutzfeldt-Jakob disease (vCJD). Further, VWF is known to form aggregates during stress conditions.

Thus there exists a need in the art to develop a stable pharmaceutical formulation comprising recombinant VWF.

SUMMARY OF THE INVENTION

The present invention provides formulations useful for lyophilization of recombinant VWF, resulting in a highly stable pharmaceutical composition. The stable pharmaceutical composition is useful as a therapeutic agent in the treatment of individuals suffering from disorders or conditions that can benefit from the administration of recombinant VWF.

In one embodiment, a stable lyophilized pharmaceutical formulation of a recombinant von Willebrand Factor (rVWF) is provided comprising: (a) a rVWF; (b) one or more buffering agents; (c) one or more amino acids; (d) one or more stabilizing agents; and (e) one or more surfactants; the rVWF comprising a polypeptide selected from the group consisting of: a) the amino acid sequence set out in SEQ ID NO: 3; b) a biologically active analog, fragment or variant of a); c) a polypeptide encoded by the polynucleotide set out in SEQ ID NO: 1; d) a biologically active analog, fragment or variant of c); and e) a polypeptide encoded by a polynucleotide that hybridizes to the polynucleotide set out in SEQ ID NO: 1 under moderately stringent hybridization conditions; the buffer is comprising of a pH buffering agent in a range of about 0.1 mM to about 500 mM and the pH is in a range of about 2.0 to about 12.0; the amino acid is at a concentration of about 1 to about 500 mM; the stabilizing agent is at a concentration of about 0.1 to about 1000 mM; and the surfactant is at a concentration of about 0.01 g/L to about 0.5 g/L.

In another embodiment, the rVWF comprises the amino acid sequence set out in SEQ ID NO: 3. In still another embodiment, the buffering agent is selected from the group consisting of citrate, glycine, histidine, HEPES, Tris and combinations of these agents. In yet another embodiment, the buffering agent is citrate. In various embodiments, the pH is in the range of about 6.0 to about 8.0, about 6.5 to about 7.5, or about 7.3. In another embodiment, the pH is about 7.3.

In another embodiment, the aforementioned amino acid is selected from the group consisting of glycine, histidine, proline, serine, alanine and arginine. In another embodiment, the amino acid is at a concentration range of about 0.5 mM to about 300 mM. In still another embodiment, the amino acid is glycine at a concentration of about 15 mM.

In one embodiment of the invention, the rVWF comprises the amino acid sequence set out in SEQ ID NO: 3; wherein the buffering agent is citrate and the pH is about 7.3; and wherein the amino acid is glycine at a concentration of about 15 mM.

In still another embodiment of the invention, the afore-mentioned one or more stabilizing agents is selected from the group consisting of mannitol, lactose, sorbitol, xylitol, sucrose, trehalose, mannose, maltose, lactose, glucose, raffinose, cellobiose, gentiobiose, isomaltose, arabinose, glucosamine, fructose and combinations of these stabilizing agents. In one embodiment, the stabilizing agents are treha-lose at a concentration of about 10 g/L mM and mannitol at a concentration of about 20 g/L.

In yet another embodiment of the invention, the afore-mentioned surfactant is selected from the group consisting of digitonin, Triton X-100, Triton X-114, TWEEN-20, TWEEN-80 and combinations of these surfactants. In still another embodiment, the surfactant is TWEEN-80 at about 0.01 g/L.

In another embodiment of the invention, the rVWF com-prises amino acid sequence set out in SEQ ID NO: 3; wherein the buffering agent is citrate at a concentration of about 15 mM at about pH 7.3; wherein the amino acid is glycine at a concentration of about 15 mM; wherein the stabilizing agents are trehalose at a concentration of about 10 g/L and mannitol at a concentration of about 20 g/L.; and wherein the surfactant is TWEEN-80 at about 0.1 g/L.

DETAILED DESCRIPTION OF THE INVENTION

Definition of Terms

Figure 1:
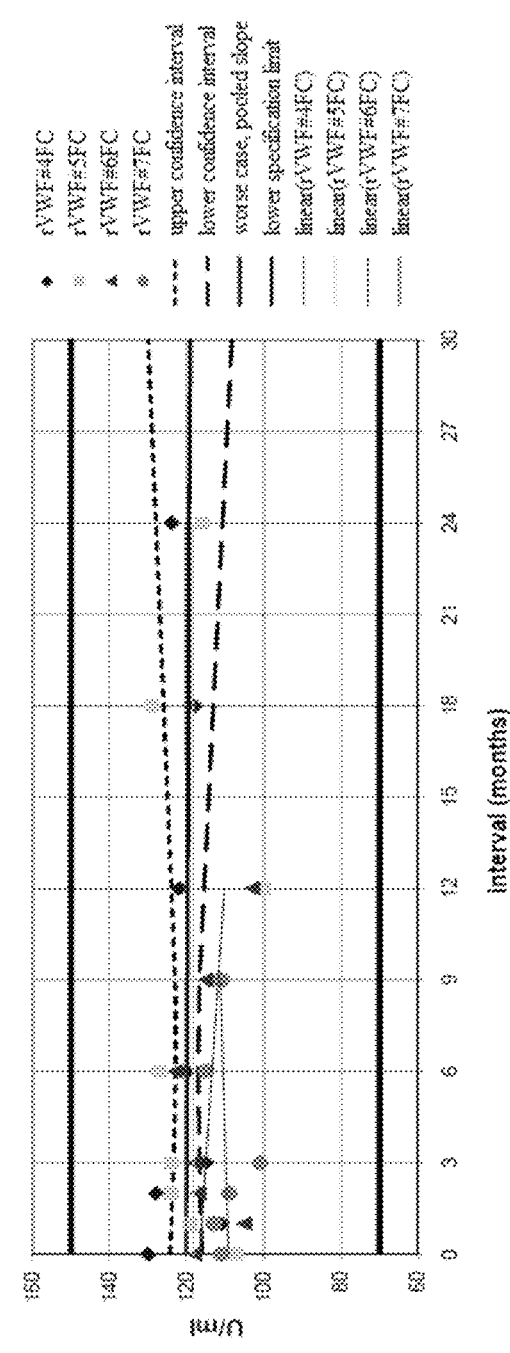
FIG. 1 shows ANCOVA analysis of pooled VWF:RCo activity in lots evaluated for stability (stored at 5° C.±3° C.).

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICRO-BIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

As used herein, the following terms have the meanings ascribed to them unless specified otherwise.

The term "comprising," with respect to a peptide com-pound, means that a compound may include additional amino acids at either or both amino and carboxy termini of the given sequence. Of course, these additional amino acids should not significantly interfere with the activity of the compound. With respect to a composition of the instant invention, the term "comprising" means that a composition may include additional components. These additional com-ponents should not significantly interfere with the activity of the composition.

The term "pharmacologically active" means that a sub-stance so described is determined to have activity that affects a medical parameter (e.g., but not limited to blood pressure, blood cell count, cholesterol level) or disease state (e.g., but not limited to cancer, autoimmune disorders).

As used herein the terms "express," "expressing" and "expression" mean allowing or causing the information in a gene or DNA sequence to become manifest, for example, producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed." An expression product can be characterized as intracellular, extracellular or secreted. The term "intracellular" means inside a cell. The term "extra-cellular" means outside a cell, such as a transmembrane protein. A substance is "secreted" by a cell if it appears in significant measure outside the cell, from somewhere on or inside the cell.

As used herein a "polypeptide" refers to a polymer composed of amino acid residues, structural variants, related naturally-occurring structural variants, and synthetic non-naturally occurring analogs thereof linked via peptide bonds. Synthetic polypeptides are prepared, for example, using an automated polypeptide synthesizer. The term "protein" typi-cally refers to large polypeptides. The term "peptide" typi-cally refers to short polypeptides.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a polypeptide, protein or analog thereof that is modified to comprise additional chemical moieties not normally a part of the molecule. Such moieties may modulate the molecule's solubility, absorp-tion, biological half-life, etc. The moieties may alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example and without limitation, in one aspect the variant is a blood clotting factor having a chemical modi-fication which confers a longer half-life in vivo to the protein. In various aspects, polypeptides are modified by glycosylation, pegylation, and/or polysialylation.

Recombinant VWF

The polynucleotide and amino acid sequences of prepro-VWF are set out in SEQ ID NO:1 and SEQ ID NO:2, respectively, and are available at GenBank Accession Nos. NM_000552 and NP_000543, respectively. The amino acid sequence corresponding to the mature VWF protein is set out in SEQ ID NO: 3 (corresponding to amino acids 764-2813 of the full length prepro-VWF amino acid sequence).

One form of useful rVWF has at least the property of in vivo-stabilizing, e.g. binding, of at least one Factor VIII (FVIII) molecule and having optionally a glycosylation pattern which is pharmacologically acceptable. Specific examples thereof include VWF without the A2 domain thus resistant to proteolysis (Lankhof et al., Thromb. Haemost. 77: 1008-1013, 1997), and a VWF fragment from Val 449 to Asn 730 including the glycoprotein lb-binding domain and binding sites for collagen and heparin (Pietu et al., Biochem. Biophys. Res. Commun. 164: 1339-1347, 1989). The determination of the ability of a VWF to stabilize at least one FVIII molecule is, in one aspect, carried out in VWF-deficient mammals according to methods known in the state in the art.

The rVWF of the present invention is produced by any method known in the art. One specific example is disclosed in WO86/06096 published on Oct. 23, 1986 and U.S. patent application Ser. No. 07/559,509, filed on Jul. 23, 1990, which is incorporated herein by reference with respect to the methods of producing recombinant VWF. Thus, methods are known in the art for (i) the production of recombinant DNA by genetic engineering, e.g. via reverse transcription of RNA and/or amplification of DNA, (ii) introducing recombinant DNA into procaryotic or eucaryotic cells by transfection, e.g. via electroporation or microinjection, (iii) cultivating the transformed cells, e.g. in a continuous or batchwise manner, (iv) expressing VWF, e.g. constitutively or upon induction, and (v) isolating the VWF, e.g. from the culture medium or by harvesting the transformed cells, in order to (vi) obtain purified rVWF, e.g. via anion exchange chromatography or affinity chromatography. A recombinant VWF is, in one aspect, made in transformed host cells using recombinant DNA techniques well known in the art. For instance, sequences coding for the polypeptide could be excised from DNA using suitable restriction enzymes. Alternatively, the DNA molecule is, in another aspect, synthesized using chemical synthesis techniques, such as the phosphoramidate method. Also, in still another aspect, a combination of these techniques is used.

The invention also provides vectors encoding polypeptides of the invention in an appropriate host. The vector comprises the polynucleotide that encodes the polypeptide operatively linked to appropriate expression control sequences. Methods of effecting this operative linking, either before or after the polynucleotide is inserted into the vector, are well known. Expression control sequences include promoters, activators, enhancers, operators, ribosomal binding sites, start signals, stop signals, cap signals, polyadenylation signals, and other signals involved with the control of transcription or translation. The resulting vector having the polynucleotide therein is used to transform an appropriate host. This transformation may be performed using methods well known in the art.

Any of a large number of available and well-known host cells are used in the practice of this invention. The selection of a particular host is dependent upon a number of factors recognized by the art, including, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all host cells are equally effective for the expression of a particular DNA sequence. Within these general guidelines, useful microbial host cells include, without limitation, bacteria, yeast and other fungi, insects, plants, mammalian (including human) cells in culture, or other hosts known in the art.

Transformed host cells are cultured under conventional fermentation conditions so that the desired compounds are expressed. Such fermentation conditions are well known in the art. Finally, the polypeptides are purified from culture media or the host cells themselves by methods well known in the art.

Depending on the host cell utilized to express a compound of the invention, carbohydrate (oligosaccharide) groups are optionally attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both N-linked and O-linked oligosaccharides is N-acetyl-neuraminic acid (referred to as sialic acid). Sialic acid is usually the terminal residue of both N-linked and O-linked oligosaccharides and, by virtue of its negative charge, in one aspect, confers acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). In other aspects, such sites are glycosylated by synthetic or semi-synthetic procedures known in the art.

Alternatively, the compounds are made by synthetic methods using, for example, solid phase synthesis techniques. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941, 763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides.

Fragments, Variants and Analogs of VWF

Methods for preparing polypeptide fragments, variants or analogs are well-known in the art.

Fragments of a polypeptide are prepared using, without limitation, enzymatic cleavage (e.g., trypsin, chymotrypsin) and also using recombinant means to generate a polypeptide fragments having a specific amino acid sequence. Polypeptide fragments may be generated comprising a region of the protein having a particular activity, such as a multimerization domain or any other identifiable VWF domain known in the art.

Methods of making polypeptide analogs are also well-known. Amino acid sequence analogs of a polypeptide can be substitutional, insertional, addition or deletion analogs. Deletion analogs, including fragments of a polypeptide, lack one or more residues of the native protein which are not essential for function or immunogenic activity. Insertional analogs involve the addition of, e.g., amino acid(s) at a non-terminal point in the polypeptide. This analog may include, for example and without limitation, insertion of an immunoreactive epitope or simply a single residue. Addition analogs, including fragments of a polypeptide, include the addition of one or more amino acids at either or both termini of a protein and include, for example, fusion proteins. Combinations of the aforementioned analogs are also contemplated.

Substitutional analogs typically exchange one amino acid of the wild-type for another at one or more sites within the protein, and may be designed to modulate one or more properties of the polypeptide without the complete loss of other functions or properties. In one aspect, substitutions are conservative substitutions. "Conservative amino acid substitution" is substitution of an amino acid with an amino acid having a side chain or a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

In one aspect, analogs are substantially homologous or substantially identical to the recombinant VWF from which they are derived. Analogs include those which retain at least some of the biological activity of the wild-type polypeptide, e.g. blood clotting activity.

Polypeptide variants contemplated include, without limitation, polypeptides chemically modified by such techniques as ubiquitination, glycosylation, including polysialation, conjugation to therapeutic or diagnostic agents, labeling, covalent polymer attachment such as pegylation (derivatization with polyethylene glycol), introduction of non-hydrolyzable bonds, and insertion or substitution by chemical synthesis of amino acids such as ornithine, which do not normally occur in human proteins. Variants retain the same or essentially the same binding properties of non-modified molecules of the invention. Such chemical modification may include direct or indirect (e.g., via a linker) attachment of an agent to the VWF polypeptide. In the case of indirect attachment, it is contemplated that the linker may be hydrolyzable or non-hydrolyzable.

Preparing pegylated polypeptide analogs will in one aspect comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions are determined based on known parameters and the desired result. For example, the larger the ratio of PEG: protein, the greater the percentage of poly-pegylated product. In some embodiments, the binding construct has a single PEG moiety at the N-terminus. Polyethylene glycol (PEG) may be attached to the blood clotting factor to, for example, provide a longer half-life in vivo. The PEG group may be of any convenient molecular weight and is linear or branched. The average molecular weight of the PEG ranges from about 2 kiloDalton ("kD") to about 100 kDa, from about 5 kDa to about 50 kDa, or from about 5 kDa to about 10 kDa. In certain aspects, the PEG groups are attached to the blood clotting factor via acylation or reductive alkylation through a natural or engineered reactive group on the PEG moiety (e.g., an aldehyde, amino, thiol, or ester group) to a reactive group on the blood clotting factor (e.g., an aldehyde, amino, or ester group) or by any other technique known in the art.

Methods for preparing polysialylated polypeptide are described in United States Patent Publication 20060160948, Femandes et Gregoriadis; Biochim. Biophys. Acta 1341: 26-34, 1997, and Saenko et al., Haemophilia 12:42-51, 2006. Briefly, a solution of colominic acid (CA) containing 0.1 M NaIO4 is stirred in the dark at room temperature to oxidize the CA. The activated CA solution is dialyzed against, e.g., 0.05 M sodium phosphate buffer, pH 7.2 in the dark and this solution was added to a rVWF solution and incubated for 18 h at room temperature in the dark under gentle shaking. Free reagents are optionally be separated from the rVWF-polysialic acid conjugate by, for example, ultrafiltration/diafiltration. Conjugation of rVWF with polysialic acid is achieved using glutaraldehyde as cross-linking reagent (Migneault et al., Biotechniques 37: 790-796, 2004).

It is further contemplated in another aspect that a polypeptide of the invention is a fusion protein with a second agent which is a polypeptide. In one embodiment, the second agent which is a polypeptide, without limitation, is an enzyme, a growth factor, an antibody, a cytokine, a chemokine, a cell-surface receptor, the extracellular domain of a cell surface receptor, a cell adhesion molecule, or fragment or active domain of a protein described above. In a related embodiment, the second agent is a blood clotting factor such as Factor VIII, Factor VII, Factor IX. The fusion protein contemplated is made by chemical or recombinant techniques well-known in the art.

It is also contemplated in another aspect that prepro-VWF and pro-VWF polypeptides will provide a therapeutic benefit in the formulations of the present invention. For example, U.S. Pat. No. 7,005,502 describes a pharmaceutical preparation comprising substantial amounts of pro-VWF that induces thrombin gemeation in vitro. In addition to recombinant, biologically active fragments, variants, or other analogs of the naturally-occurring mature VWF, the present invention contemplates the use of recombinant biologically active fragments, variants, or analogs of the prepro-VWF (set out in SEQ ID NO:2) or pro-VWF polypeptides (amino acid residues 23 to 764 of SEQ ID NO: 2) in the formulations described herein.

Polynucleotides encoding fragments, variants and analogs may be readily generated by a worker of skill to encode biologically active fragments, variants, or analogs of the naturally-occurring molecule that possess the same or similar biological activity to the naturally-occurring molecule. In various aspects, these polynucleotides are prepared using PCR techniques, digestion/ligation of DNA encoding molecule, and the like. Thus, one of skill in the art will be able to generate single base changes in the DNA strand to result in an altered codon and a missense mutation, using any method known in the art, including, but not limited to site-specific mutagenesis. As used herein, the phrase "moderately stringent hybridization conditions" means, for example, hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47-9.51 in Molecular Cloning, Cold Spring Harbor Laboratory Press, Cold Spring Harbor, New York (1989).

Lyophilization

In one aspect, the formulations comprising a VWF polypeptide of the invention are lyophilized prior to administration. Lyophilization is carried out using techniques common in the art and should be optimized for the composition being developed [Tang et al., Pharm Res. 21:191-200, (2004) and Chang et al., Pharm Res. 13:243-9 (1996)].

A lyophilization cycle is, in one aspect, composed of three steps: freezing, primary drying, and secondary drying [A. P. Mackenzie, Phil Trans R Soc London, Ser B, Biol 278:167 (1977)]. In the freezing step, the solution is cooled to initiate ice formation. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and at an elevated shelf temperature. The process produces a material known as a lyophilized cake. Thereafter the cake can be reconstituted with either sterile water or suitable diluent for injection.

The lyophilization cycle not only determines the final physical state of excipients but also affects other parameters such as reconstitution time, appearance, stability and final moisture content. The composition structure in the frozen state proceeds through several transitions (e.g., glass transitions, wettings, and crystallizations) that occur at specific temperatures and the structure may be used to understand and optimize the lyophilization process. The glass transition temperature (Tg and/or Tg') can provide information about the physical state of a solute and can be determined by differential scanning calorimetry (DSC). Tg and Tg' are an important parameter that must be taken into account when designing the lyophilization cycle. For example, Tg' is important for primary drying. Furthermore, in the dried state, the glass transition temperature provides information on the storage temperature of the final product.

Formulations and Excipients in General

Excipients are additives that either impart or enhance the stability and delivery of a drug product (e.g., protein). Regardless of the reason for their inclusion, excipients are an integral component of a formulation and therefore need to be safe and well tolerated by patients. For protein drugs, the choice of excipients is particularly important because they can affect both efficacy and immunogenicity of the drug. Hence, protein formulations need to be developed with appropriate selection of excipients that afford suitable stability, safety, and marketability.

A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization. A comparison of the excipient components contemplated for liquid and lyophilized protein formulations is provided in Table A.

TABLE A

Excipient components of lyophilized protein formulations

| Excipient component | Function in lyophilized formulation |
| --- | --- |
| Buffer | Maintain pH of formulation during lyophilization and upon reconstitution |

TABLE A-continued

Excipient components of lyophilized protein formulations

| Excipient component | Function in lyophilized formulation |
| --- | --- |
| Tonicity agent/stabilizer | Stabilizers include cryo and lyoprotectants Examples include Polyols, sugars and polymers Cryoprotectants protect proteins from freezing stresses Lyoprotectants stabilize proteins in the freeze-dried state |
| Bulking agent | Used to enhance product elegance and to prevent blowout Provides structural strength to the lyo cake Examples include mannitol and glycine |
| Surfactant | Employed if aggregation during the lyophilization process is an issue May serve to reduce reconstitution times Examples include polysorbate 20 and 80 |
| Anti-oxidant | Usually not employed, molecular reactions in the lyo cake are greatly retarded |
| Metal ions/chelating agent | May be included if a specific metal ion is included only as a co-factor or where the metal is required for protease activity Chelating agents are generally not needed in lyo formulations |
| Preservative | For multi-dose formulations only Provides protection against microbial growth in formulation Is usually included in the reconstitution diluent (e.g. bWFI) |

The principal challenge in developing formulations for proteins is stabilizing the product against the stresses of manufacturing, shipping and storage. The role of formulation excipients is to provide stabilization against these stresses. Excipients are also be employed to reduce viscosity of high concentration protein formulations in order to enable their delivery and enhance patient convenience. In general, excipients can be classified on the basis of the mechanisms by which they stabilize proteins against various chemical and physical stresses. Some excipients are used to alleviate the effects of a specific stress or to regulate a particular susceptibility of a specific protein. Other excipients have more general effects on the physical and covalent stabilities of proteins. The excipients described herein are organized either by their chemical type or their functional role in formulations. Brief descriptions of the modes of stabilization are provided when discussing each excipient type.

Given the teachings and guidance provided herein, those skilled in the art will know what amount or range of excipient can be included in any particular formulation to achieve a biopharmaceutical formulation of the invention that promotes retention in stability of the biopharmaceutical (e.g., a protein). For example, the amount and type of a salt to be included in a biopharmaceutical formulation of the invention is selected based on the desired osmolality (i.e., isotonic, hypotonic or hypertonic) of the final solution as well as the amounts and osmolality of other components to be included in the formulation.

By way of example, inclusion of about 5% sorbitol can achieve isotonicity while about 9% of a sucrose excipient is needed to achieve isotonicity. Selection of the amount or range of concentrations of one or more excipients that can be included within a biopharmaceutical formulation of the invention has been exemplified above by reference to salts, polyols and sugars. However, those skilled in the art will understand that the considerations described herein and further exemplified by reference to specific excipients are equally applicable to all types and combinations of excipients including, for example, salts, amino acids, other tonicity agents, surfactants, stabilizers, bulking agents, cryoprotectants, lyoprotectants, anti-oxidants, metal ions, chelating agents and/or preservatives.

Further, where a particular excipient is reported in molar concentration, those skilled in the art will recognize that the equivalent percent (%) w/v (e.g., (grams of substance in a solution sample/mL of solution)×100%) of solution is also contemplated.

Of course, a person having ordinary skill in the art would recognize that the concentrations of the excipients described herein share an interdependency within a particular formulation. By way of example, the concentration of a bulking agent may be lowered where, e.g., there is a high protein concentration or where, e.g., there is a high stabilizing agent concentration. In addition, a person having ordinary skill in the art would recognize that, in order to maintain the isotonicity of a particular formulation in which there is no bulking agent, the concentration of a stabilizing agent would be adjusted accordingly (i.e., a "tonicifying" amount of stabilizer would be used). Common excipients are known in the art and can be found in Powell et al., Compendium of Excipients fir Parenteral Formulations (1998), PDA J. Pharm. Sci. Technology, 52:238-311.

Buffers and Buffering Agents

The stability of a pharmacologically active protein formulation is usually observed to be maximal in a narrow pH range. This pH range of optimal stability needs to be identified early during pre-formulation studies. Several approaches, such as accelerated stability studies and calorimetric screening studies, are useful in this endeavor (Remmele R. L. Jr., et al., *Biochemistry*, 38(16): 5241-7 (1999)). Once a formulation is finalized, the protein must be manufactured and maintained throughout its shelf-life. Hence, buffering agents are almost always employed to control pH in the formulation.

The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

Several factors need to be considered when choosing a buffer. First and foremost, the buffer species and its concentration need to be defined based on its pKa and the desired formulation pH. Equally important is to ensure that the buffer is compatible with the protein and other formulation excipients, and does not catalyze any degradation reactions. A third important aspect to be considered is the sensation of stinging and irritation the buffer may induce upon administration. For example, citrate is known to cause stinging upon injection (Laursen T, et al., *Basic Clin Pharmacol Toxicol.*, 98(2): 218-21 (2006)). The potential for stinging and irritation is greater for drugs that are administered via the subcutaneous (SC) or intramuscular (IM) routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. One has to be particularly careful about potassium ions administered in the form of the potassium phosphate buffer, which can induce cardiovascular effects in a patient (Hollander-Rodriguez J C, et al., *Am. Fam. Physician.*, 73(2): 283-90 (2006)).

Buffers for lyophilized formulations need additional consideration. Some buffers like sodium phosphate can crystallize out of the protein amorphous phase during freezing resulting in shifts in pH. Other common buffers such as acetate and imidazole may sublime or evaporate during the lyophilization process, thereby shifting the pH of formulation during lyophilization or after reconstitution.

The buffer system present in the compositions is selected to be physiologically compatible and to maintain a desired pH of the pharmaceutical formulation. In one embodiment, the pH of the solution is between pH 2.0 and pH 12.0. For example, the pH of the solution may be 2.0, 2.3, 2.5, 2.7, 3.0, 3.3, 3.5, 3.7, 4.0, 4.3, 4.5, 4.7, 5.0, 5.3, 5.5, 5.7, 6.0, 6.3, 6.5, 6.7, 7.0, 7.3, 7.5, 7.7, 8.0, 8.3, 8.5, 8.7, 9.0, 9.3, 9.5, 9.7, 10.0, 10.3, 10.5, 10.7, 11.0, 11.3, 11.5, 11.7, or 12.0.

The pH buffering compound may be present in any amount suitable to maintain the pH of the formulation at a predetermined level. In one embodiment, the pH buffering concentration is between 0.1 mM and 500 mM (1 M). For example, it is contemplated that the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 25, 30, 40, 50, 60, 70, 80, 90, 100, 200, or 500 mM.

Exemplary pH buffering agents used to buffer the formulation as set out herein include, but are not limited to organic acids, glycine, histidine, glutamate, succinate, phosphate, acetate, citrate, Tris, HEPES, and amino acids or mixtures of amino acids, including, but not limited to aspartate, histidine, and glycine. In one embodiment of the present invention, the buffering agent is citrate.

Stabilizers and Bulking Agents

In one aspect of the present pharmaceutical formulations, a stabilizer (or a combination of stabilizers) is added to prevent or reduce storage-induced aggregation and chemical degradation. A hazy or turbid solution upon reconstitution indicates that the protein has precipitated or at least aggregated. The term "stabilizer" means an excipient capable of preventing aggregation or physical degradation, including chemical degradation (for example, autolysis, deamidation, oxidation, etc.) in an aqueous state. Stabilizers contemplated include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, sodium chloride, [Carpenter et al., Develop. Biol. Standard 74:225, (1991)]. In the present formulations, the stabilizer is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM. In one embodiment f the present invention, mannitol and trehalose are used as stabilizing agents.

If desired, the formulations also include appropriate amounts of bulking and osmolarity regulating agents. Bulking agents include, for example and without limitation, mannitol, glycine, sucrose, polymers such as dextran, polyvinylpyrolidone, carboxymethylcellulose, lactose, sorbitol, trehalose, or xylitol. In one embodiment, the bulking agent is mannitol. The bulking agent is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM.

Surfactants

Proteins have a high propensity to interact with surfaces making them susceptible to adsorption and denaturation at air-liquid, vial-liquid, and liquid-liquid (silicone oil) interfaces. This degradation pathway has been observed to be inversely dependent on protein concentration and results in either the formation of soluble and insoluble protein aggregates or the loss of protein from solution via adsorption to surfaces. In addition to container surface adsorption, surface-induced degradation is exacerbated with physical agitation, as would be experienced during shipping and handling of the product.

Surfactants are commonly used in protein formulations to prevent surface-induced degradation. Surfactants are amphipathic molecules with the capability of out-competing proteins for interfacial positions. Hydrophobic portions of the surfactant molecules occupy interfacial positions (e.g., air/liquid), while hydrophilic portions of the molecules remain oriented towards the bulk solvent. At sufficient concentrations (typically around the detergent's critical micellar concentration), a surface layer of surfactant molecules serve to prevent protein molecules from adsorbing at the interface. Thereby, surface-induced degradation is minimized. Surfactants contemplated herein include, without limitation, fatty acid esters of sorbitan polyethoxylates, i.e. polysorbate 20 and polysorbate 80. The two differ only in the length of the aliphatic chain that imparts hydrophobic character to the molecules, C-12 and C-18, respectively. Accordingly, polysorbate-80 is more surface-active and has a lower critical micellar concentration than polysorbate-20.

Detergents can also affect the thermodynamic conformational stability of proteins. Here again, the effects of a given detergent excipient will be protein specific. For example, polysorbates have been shown to reduce the stability of some proteins and increase the stability of others. Detergent destabilization of proteins can be rationalized in terms of the hydrophobic tails of the detergent molecules that can engage in specific binding with partially or wholly unfolded protein states. These types of interactions could cause a shift in the conformational equilibrium towards the more expanded protein states (i.e. increasing the exposure of hydrophobic portions of the protein molecule in complement to binding polysorbate). Alternatively, if the protein native state exhibits some hydrophobic surfaces, detergent binding to the native state may stabilize that conformation.

Another aspect of polysorbates is that they are inherently susceptible to oxidative degradation. Often, as raw materials, they contain sufficient quantities of peroxides to cause oxidation of protein residue side-chains, especially methionine. The potential for oxidative damage arising from the addition of stabilizer emphasizes the point that the lowest effective concentrations of excipients should be used in formulations. For surfactants, the effective concentration for a given protein will depend on the mechanism of stabilization.

Surfactants are also added in appropriate amounts to prevent surface related aggregation phenomenon during freezing and drying [Chang, B, J. Pharm. Sci. 85:1325, (1996)]. Thus, exemplary surfactants include, without limitation, anionic, cationic, nonionic, zwitterionic, and amphoteric surfactants including surfactants derived from naturally-occurring amino acids. Anionic surfactants include, but are not limited to, sodium lauryl sulfate, dioctyl sodium sulfosuccinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. Surfactants also include, but are not limited to lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as dioleyl phosphatidyl choline (DOPC), dimyristoylphosphatidyl glycerol (DMPG), dimyristoylphosphatidyl choline (DMPC), and (dioleyl phosphatidyl glycerol) DOPG; sucrose fatty acid ester, methyl cellulose and carboxymethyl cellulose. Compositions comprising these surfactants, either individually or as a mixture in different ratios, are therefore further provided. In one embodiment of the present invention, the surfactant is TWEEN-80. In the present formulations, the surfactant is incorporated in a concentration of about 0.01 to about 0.5 g/L. In formulations provided, the surfactant concentration is 0.005, 0.01, 0.02, 0.03, 0.05, 0.06, 0.07, 0.08, 0.09, 0.1, 0.2, 0.3, 0.4, 0.5, 0.6, 0.7, 0.8, 0.9 or 1.0 g/L.

Salts

Salts are often added to increase the ionic strength of the formulation, which can be important for protein solubility, physical stability, and isotonicity. Salts can affect the physical stability of proteins in a variety of ways. Ions can stabilize the native state of proteins by binding to charged residues on the protein's surface. Alternatively, salts can stabilize the denatured state by binding to peptide groups along the protein backbone (—CONH—). Salts can also stabilize the protein native conformation by shielding repulsive electrostatic interactions between residues within a protein molecule. Salts in protein formulations can also shield attractive electrostatic interactions between protein molecules that can lead to protein aggregation and insolubility. In formulations provided, the salt concentration is between 0.1, 1, 10, 20, 30, 40, 50, 80, 100, 120, 150, 200, 300, and 500 mM.

Other Common Excipient Components

Amino Acids

Amino acids have found versatile use in protein formulations as buffers, bulking agents, stabilizers and antioxidants. Thus, in one aspect histidine and glutamic acid are employed to buffer protein formulations in the pH range of 5.5-6.5 and 4.0-5.5 respectively. The imidazole group of histidine has a pKa=6.0 and the carboxyl group of glutamic acid side chain has a pKa of 4.3 which makes these amino acids suitable for buffering in their respective pH ranges. Glutamic acid is particularly useful in such cases. Histidine is commonly found in marketed protein formulations, and this amino acid provides an alternative to citrate, a buffer known to sting upon injection. Interestingly, histidine has also been reported to have a stabilizing effect, with respect to aggregation when used at high concentrations in both liquid and lyophilized presentations (Chen B, et al., *Pharm Res.*, 20(12): 1952-60 (2003)). Histidine was also observed by others to reduce the viscosity of a high protein concentration formulation. However, in the same study, the authors observed increased aggregation and discoloration in histidine containing formulations during freeze-thaw studies of the antibody in stainless steel containers. Another note of caution with histidine is that it undergoes photo-oxidation in the presence of metal ions (Tomita M, et al., *Biochemistry*, 8(12): 5149-60 (1969)). The use of methionine as an antioxidant in formulations appears promising; it has been observed to be effective against a number of oxidative stresses (Lam X M, et al., *J Pharm Sci.*, 86(11): 1250-5 (1997)).

In various aspects, formulations are provided which include one or more of the amino acids glycine, proline, serine, arginine and alanine have been shown to stabilize proteins by the mechanism of preferential exclusion. Glycine is also a commonly used bulking agent in lyophilized formulations. Arginine has been shown to be an effective agent in inhibiting aggregation and has been used in both liquid and lyophilized formulations.

In formulations provided, the amino acid concentration is between 0.1, 1, 10, 20, 30, 40, 50, 80, 100, 120, 150, 200, 300, and 500 mM. In one embodiment of the present invention, the amino acid is glycine.

Antioxidants

Oxidation of protein residues arises from a number of different sources. Beyond the addition of specific antioxidants, the prevention of oxidative protein damage involves the careful control of a number of factors throughout the manufacturing process and storage of the product such as atmospheric oxygen, temperature, light exposure, and chemical contamination. The invention therefore contemplates the use of the pharmaceutical antioxidants including, without limitation, reducing agents, oxygen/free-radical scavengers, or chelating agents. Antioxidants in therapeutic protein formulations are, in one aspect, water-soluble and remain active throughout the product shelf-life. Reducing agents and oxygen/free-radical scavengers work by ablating active oxygen species in solution. Chelating agents such as EDTA are effective by binding trace metal contaminants that promote free-radical formation. For example, EDTA was utilized in the liquid formulation of acidic fibroblast growth factor to inhibit the metal ion catalyzed oxidation of cysteine residues.

In addition to the effectiveness of various excipients to prevent protein oxidation, the potential for the antioxidants themselves to induce other covalent or physical changes to the protein is of concern. For example, reducing agents can cause disruption of intramolecular disulfide linkages, which can lead to disulfide shuffling. In the presence of transition metal ions, ascorbic acid and EDTA have been shown to promote methionine oxidation in a number of proteins and peptides (Akers M J, and Defelippis M R. Peptides and Proteins as Parenteral Solutions. In: Pharmaceutical Formulation Development of Peptides and Proteins. Sven Frokjaer, Lars Hovgaard, editors. Pharmaceutical Science. Taylor and Francis, UK (1999)); Fransson J. R., *J. Pharm.* Sci. 86(9): 4046-1050 (1997); Yin J, et al., *Pharm Res.,* 21(12): 2377-83 (2004)). Sodium thiosulfate has been reported to reduce the levels of light and temperature induced methionine-oxidation in rhuMab HER2; however, the formation of a thiosulfate-protein adduct was also reported in this study (Lam X M, Yang J Y, et al., J Pharm Sci. 86(11): 1250-5 (1997)). Selection of an appropriate antioxidant is made according to the specific stresses and sensitivities of the protein. Antioxidants contemplated in certain aspects include, without limitation, reducing agents and oxygen/free-radical scavengers, EDTA, and sodium thiosulfate.

Metal Ions

In general, transition metal ions are undesired in protein formulations because they can catalyze physical and chemical degradation reactions in proteins. However, specific metal ions are included in formulations when they are co-factors to proteins and in suspension formulations of proteins where they form coordination complexes (e.g., zinc suspension of insulin). Recently, the use of magnesium ions (10-120 mM) has been proposed to inhibit the isomerization of aspartic acid to isoaspartic acid (WO 2004039337).

Two examples where metal ions confer stability or increased activity in proteins are human deoxyribonuclease (rhDNase, Pulmozyme®), and Factor VIII. In the case of rhDNase, $Ca^{+2}$ ions (up to 100 mM) increased the stability of the enzyme through a specific binding site (Chen B, et al., *J Pharm Sci.,* 88(4): 477-82 (1999)). In fact, removal of calcium ions from the solution with EGTA caused an increase in deamidation and aggregation. However, this effect was observed only with $Ca^{+2}$ ions; other divalent cations $Mg^{+2}$, $Mn^{+2}$ and $Zn^{+2}$ were observed to destabilize rhDNase. Similar effects were observed in Factor VIII. $Ca^{+2}$ and $Sr^{+2}$ ions stabilized the protein while others like $Mg^{+2}$, $Mn^{+2}$ and $Zn^{+2}$, $Cu^{+2}$ and $Fe^{+2}$ destabilized the enzyme (Fatouros, A., et al., *Int. J. Pharm.,* 155, 121-131 (1997). In a separate study with Factor VIII, a significant increase in aggregation rate was observed in the presence of $Al^{+3}$ ions (Derrick T S, et al., *J. Pharm. Sci.,* 93(10): 2549-57 (2004)). The authors note that other excipients like buffer salts are often contaminated with $Al^{+3}$ ions and illustrate the need to use excipients of appropriate quality in formulated products.

Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include, without limitation, benzyl alcohol, phenol and m-cresol. Although preservatives have a long history of use, the development of protein formulations that includes preservatives can be challenging. Preservatives almost always have a destabilizing effect (aggregation) on proteins, and this has become a major factor in limiting their use in multi-dose protein formulations (Roy S, et al., J Pharm Sci., 94(2): 382-96 (2005)).

To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin® (liquid, Novo Nordisk), Nutropin AQ® (liquid, Genentech) & Genotropin (lyophilized—dual chamber cartridge, Pharmacia & Upjohn) contain phenol while Somatrope® (Eli Lilly) is formulated with m-cresol.

Several aspects need to be considered during the formulation development of preserved dosage forms. The effective preservative concentration in the drug product must be optimized. This requires testing a given preservative in the dosage form with concentration ranges that confer antimicrobial effectiveness without compromising protein stability. For example, three preservatives were successfully screened in the development of a liquid formulation for interleukin-1 receptor (Type I), using differential scanning calorimetry (DSC). The preservatives were rank ordered based on their impact on stability at concentrations commonly used in marketed products (Remmele R L Jr., et al., *Pharm Res.,* 15(2): 200-8 (1998)).

Development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein significantly minimizing the associated stability risks. With liquid formulations, preservative effectiveness and stability have to be maintained over the entire product shelf-life (~18-24 months). An important point to note is that preservative effectiveness has to be demonstrated in the final formulation containing the active drug and all excipient components.

Some preservatives can cause injection site reactions, which is another factor that needs consideration when choosing a preservative. In clinical trials that focused on the evaluation of preservatives and buffers in Norditropin, pain perception was observed to be lower in formulations containing phenol and benzyl alcohol as compared to a formulation containing m-cresol (Kappelgaard A. M., Horm Res. 62 Suppl 3:98-103 (2004)). Interestingly, among the commonly used preservative, benzyl alcohol possesses anesthetic properties (Minogue S C, and Sun D A., *Anesth Analg.*, 100(3): 683-6 (2005)). In various aspects the use of preservatives provide a benefit that outweighs any side effects.

Methods of Preparation

The present invention further contemplates methods for the preparation of pharmaceutical formulations.

The present methods further comprise one or more of the following steps: adding a stabilizing agent as described herein to said mixture prior to lyophilizing, adding at least one agent selected from a bulking agent, an osmolarity regulating agent, and a surfactant, each of which as described herein, to said mixture prior to lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration [Chen, Drug Development and Industrial Pharmacy, 18:1311-1354 (1992)]. Accordingly, methods are provided for preparation of reconstituted rVWF compositions comprising the step of adding a diluent to a lyophilized rVWFcomposition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

Administration

To administer compositions to human or test animals, in one aspect, the compositions comprises one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The pharmaceutical formulations are administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Single or multiple administrations of the compositions are carried out with the dose levels and pattern being selected by the treating physician. For the prevention or treatment of disease, the appropriate dosage depends on the type of disease to be treated, as defined above, the severity and course of the disease, whether drug is administered for preventive or therapeutic purposes, previous therapy, the patient's clinical history and response to the drug, and the discretion of the attending physician.

Kits

As an additional aspect, the invention includes kits which comprise one or more lyophilized compositions packaged in a manner which facilitates their use for administration to subjects. In one embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none). In one embodiment, the kit contains a first container having a therapeutic protein or peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

Dosages

The dosage regimen involved in a method for treating a condition described herein will be determined by the attending physician, considering various factors which modify the action of drugs, e.g. the age, condition, body weight, sex and diet of the patient, the severity of any infection, time of administration and other clinical factors. By way of example, a typical dose of a recombinant VWF of the present invention is approximately 50 U/kg, equal to 500 µg/kg.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed. (1990, Mack Publishing Co., Easton, PA 18042) pages 1435-1712, the disclosure of which is hereby incorporated by reference. Such formulations influence the

20

Example 1

Shaking Experiments

In order to determine the amount of precipitation of rVWF in various formulations, the extent of aggregation of rVWF following turbulent shaking was tested under a variety of conditions.

As shown in Table 1 below, various rVWF formulations were assessed in a 20 mM citrate buffer, pH 7.3. Shaking experiments were designed to simulate mechanical stress conditions. 1-2 ml of each formulation was shaken with a laboratory shaker for 10 minutes at 1200 rpm.

TABLE 1

| Lyo 25 | Lysine | Histidine | Glycine | Serine | Mannitol | PEG 1500 | Tween 80 | Sucrose | Trehalose | Raffinose |
|---|---|---|---|---|---|---|---|---|---|---|
| 18 | 30 mM | | | | 5 g/L | | | | | |
| 19 | | 30 mM | | | 5 g/L | | | | | |
| 20 | | | 30 mM | | 5 g/L | | | | | |
| 21 | | | | 30 mM | 5 g/L | | | | | |
| 22 | 30 mM | | | | | 5 g/L | | | | |
| 23 | | 30 mM | | | | 5 g/L | | | | |
| 24 | | | 30 mM | | | 5 g/L | | | | |
| 25 | | | | 30 mM | | 5 g/L | | | | |
| 26 | 30 mM | | | | | | 0.1 g/L | | | |
| 27 | | 30 mM | | | | | 0.1 g/L | | | |
| 28 | | | 30 mM | | | | 0.1 g/L | | | |
| 29 | | | | 30 mM | | | 0.1 g/L | | | |
| 30 | 30 mM | | | | 5 g/L | 5 g/L | | | | |
| 31 | | 30 mM | | | 5 g/L | 5 g/L | | | | |
| 32 | | | 30 mM | | 5 g/L | 5 g/L | | | | |
| 33 | | | | 30 mM | 5 g/L | 5 g/L | | | | |
| 34 | 30 mM | | | | 5 g/L | | 0.1 g/L | | | |
| 35 | | 30 mM | | | 5 g/L | | 0.1 g/L | | | |
| 36 | | | 30 mM | | 5 g/L | | 0.1 g/L | | | |
| 37 | | | | 30 mM | 5 g/L | | 0.1 g/L | | | |
| 38 | 30 mM | | | | 5 g/L | 5 g/L | 0.1 g/L | | | |
| 39 | | 30 mM | | | 5 g/L | 5 g/L | 0.1 g/L | | | |
| 40 | | | 30 mM | | 5 g/L | 5 g/L | 0.1 g/L | | | |
| 41 | | | | 30 mM | 5 g/L | 5 g/L | 0.1 g/L | | | |
| 42 | | | | | 5 g/L | | | | | |
| 43 | | | | | | | | 5 g/L | | |
| 44 | | | | | | | | | 5 g/L | |
| 45 | | | | | | | | | | 5 g/L |
| 46 | | | | | 5 g/L | 5 g/L | | | | |
| 47 | | | | | | 5 g/L | | 5 g/L | | |
| 48 | | | | | | 5 g/L | | | 5 g/L | |
| 49 | | | | | | 5 g/L | | | | 5 g/L |
| 50 | | | | | 5 g/L | | 0.1 g/L | | | |
| 51 | | | | | | | 0.1 g/L | 5 g/L | | |
| 52 | | | | | | | 0.1 g/L | | 5 g/L | |
| 53 | | | | | | | 0.1 g/L | | | 5 g/L | physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

The following examples are not intended to be limiting but only exemplary of specific embodiments of the invention.

The assessment of the visible VWF aggregates was done according to the scheme shown below. "Visible aggregates," in most cases, are gelatinous fibers ranging in size from about 100 nm to 1-2 cm.

| SCHEME | |
|---|---|
| Particles | |
| A | no particles |
| B | several particles, rarely visible (dots) |
| B1 | many particles, rarely visible (dots) |
| C | several particles, easily visible (fibers) |
| D | many particles, easily visible (fibers) |
| E | visible particles (>1 mm fibers) |
| E1 | fluffy white precipitate (swims on the surface) |
| E2 | jellyfish |

The results of the shaking experiments are shown in Table 2, below.

TABLE 2

| Lyo 25 Samples | Lysine | Histidine | Glycine | Serine | Mannitol | PEG 1500 | Tween 80 | Shaking 1-2 mL 1200 rpm 30 min |
|---|---|---|---|---|---|---|---|---|
| 18 | 30 mM | | | | 5 g/L | | | E1 |
| 19 | | 30 mM | | | 5 g/L | | | E1 |
| 20 | | | 30 mM | | 5 g/L | | | E1 |
| 21 | | | | 30 mM | 5 g/L | | | E1 |
| 22 | 30 mM | | | | | 5 g/L | | E1 |
| 23 | | 30 mM | | | | 5 g/L | | E1 |
| 24 | | | 30 mM | | | 5 g/L | | E1 |
| 25 | | | | 30 mM | | 5 g/L | | E1 |
| 26 | 30 mM | | | | | | 0.1 g/L | E2 big |
| 27 | | 30 mM | | | | | 0.1 g/L | E2 big |
| 28 | | | 30 mM | | | | 0.1 g/L | E2 ~6 mm |
| 29 | | | | 30 mM | | | 0.1 g/L | E2 ~3 mm |
| 30 | 30 mM | | | | 5 g/L | 5 g/L | | E1 |
| 31 | | 30 mM | | | 5 g/L | 5 g/L | | E1 |
| 32 | | | 30 mM | | 5 g/L | 5 g/L | | E1 |
| 33 | | | | 30 mM | 5 g/L | 5 g/L | | E1 |
| 34 | 30 mM | | | | 5 g/L | | 0.1 g/L | B1 |
| 35 | | 30 mM | | | 5 g/L | | 0.1 g/L | B |
| 36 | | | 30 mM | | 5 g/L | | 0.1 g/L | E2 big |
| 37 | | | | 30 mM | 5 g/L | | 0.1 g/L | E2 big |
| 38 | 30 mM | | | | 5 g/L | 5 g/L | 0.1 g/L | D |
| 39 | | 30 mM | | | 5 g/L | 5 g/L | 0.1 g/L | D |
| 40 | | | 30 mM | | 5 g/L | 5 g/L | 0.1 g/L | B |
| 41 | | | | 30 mM | 5 g/L | 5 g/L | 0.1 g/L | B |

In summary, the shaking experiments described above indicate that formulations containing TWEEN-80® and Mannitol provide the best results (i.e., the least amount of aggregation).

Example 2

Freeze-Thaw Experiments

Freeze-thaw experiments were designed to assess the impact of stress caused by repeated freezing and thawing. In addition to the formulations described above for the shaking experiments (Table 1), the following formulations were assessed (Table 3 and Table 4).

TABLE 3

| Lyo 25 Samples | Mannitol | PEG 1500 | Tween 80 | Sucrose | Trehalose | Raffinose |
|---|---|---|---|---|---|---|
| 42 | 5 g/L | | | | | |
| 43 | | | | 5 g/L | | |

TABLE 3-continued

| Lyo 25 Samples | Mannitol | PEG 1500 | Tween 80 | Sucrose | Trehalose | Raffinose |
|---|---|---|---|---|---|---|
| 44 | | | | | 5 g/L | |
| 45 | | | | | | 5 g/L |
| 46 | 5 g/L | 5 g/L | | | | |
| 47 | | 5 g/L | | | | |
| 48 | | 5 g/L | | | | |
| 49 | | 5 g/L | | | | |
| 50 | 5 g/L | | 0.1 g/L | | | |
| 51 | | | 0.1 g/L | 5 g/L | | |
| 52 | | | 0.1 g/L | | 5 g/L | |
| 53 | | | 0.1 g/L | | | 5 g/L |

TABLE 4

| Lyo 25 Samples | Lysine | Histidine | Glycine | Serine | Mannitol | PEG 1500 | Tween-80 | Sucrose | Trehalose | Raffinose |
|---|---|---|---|---|---|---|---|---|---|---|
| 76 | | | | | 20 g/L | | 0.2 g/L | 20 g/L | | |
| 77 | | | | | 20 g/L | | 0.2 g/L | | 10 g/L | |
| 78 | | | | | 20 g/L | | 0.2 g/L | | | 10 g/L |
| 79 | | 15 mM | | | 20 g/L | | 0.2 g/L | 20 g/L | | |
| 80 | | 15 mM | | | 20 g/L | | 0.2 g/L | | 10 g/L | |
| 81 | | 15 mM | | | 20 g/L | | 0.2 g/L | | | 10 g/L |
| 82 | | 15 mM | 15 mM | | 20 g/L | | 0.2 g/L | 20 g/L | | |
| 83 | | 15 mM | 15 mM | | 20 g/L | | 0.2 g/L | | 10 g/L | |
| 84 | | 15 mM | 15 mM | | 20 g/L | | 0.2 g/L | | | 10 g/L |
| 85 | | 15 mM | 15 mM | | 20 g/L | 5 g/L | 0.2 g/L | | | |
| 86 | | 15 mM | 15 mM | | 20 g/L | 5 g/L | 0.2 g/L | | 10 g/L | |
| 87 | | 15 mM | 15 mM | | 20 g/L | 15 g/L | 0.2 g/L | | 10 g/L | |
| 88 | | 15 mM | 15 mM | | 20 g/L | | 0.2 g/L | | | 5 g/L |
| 89 | | 15 mM | 15 mM | | 20 g/L | | 0.2 g/L | | | 15 g/L |

TABLE 4-continued

| Lyo 25 Samples | Lysine | Histidine | Glycine | Serine | Mannitol | PEG 1500 | Tween-80 | Sucrose | Trehalose | Raffinose |
|---|---|---|---|---|---|---|---|---|---|---|
| 90 | | 15 mM | | | 20 g/L | | 0.2 g/L | | | 15 g/L |
| 92 | | 15 mM | 15 mM | | 20 g/L | | 0.2 g/L | | 10 g/L | |
| 93 | 30 mM | | | | 20 g/L | | 0.2 g/L | | 10 g/L | |
| 94 | | | 30 mM | | 20 g/L | | 0.2 g/L | | 10 g/L | |
| 95 | | | | 30 mM | 20 g/L | | 0.2 g/L | | 10 g/L | |
| 96 | | | | 30 mM | 20 g/L | | 0.2 g/L | | 10 g/L | |
| 97 | | 15 mM | | | 20 g/L | | 0.2 g/L | | 10 g/L | |
| 98 | | 15 mM | 15 mM | | 20 g/L | | 0.2 g/L | | 10 g/L | |
| 99 | | 15 mM | 15 mM | | 20 g/L | | 0.2 g/L | | 5 g/L | |
| 100 | | 15 mM | | | 20 g/L | | 0.2 g/L | | 10 g/L | |
| | | 15 mM | | | 20 g/L | | 0.2 g/L | | 10 g/L | |

15

All formulations were frozen at −20° C. in a freezer for approximately 1 hour and then thawed at room temperature. The results are shown in Table 5 below.

TABLE 5

| Lyo 25 Samples | Lysine | Histidine | Glycine | Serine | Mannitol | PEG 1500 | Tween-80 | Sucrose | Trehalose | Raffinose | Freeze/Thaw (4 times) | Freeze/Thaw (~10 times) |
|---|---|---|---|---|---|---|---|---|---|---|---|---|
| 18 | 30 mM | | | | 5 g/L | | | | | | E1 | 15 |
| 19 | | 30 mM | | | 5 g/L | | | | | | E1 | 19 |
| 20 | | | 30 mM | | 5 g/L | | | | | | C | 20 |
| 21 | | | | 30 mM M | 5 g/L | | | | | | C | 21 |
| 22 | 30 mM | | | | | | | | | | C | 22 |
| 23 | | 30 mM | | | | | | | | | C/B1 | 23 |
| 24 | | | 30 mM | | | | | | | | C | 24 |
| 25 | | | | 30 mM M | | | | | | | C | 25 |
| 26 | 30 mM | | | | | | 0.1 g/L | | | | B | 26 |
| 27 | | 30 mM | | | | | 0.1 g/L | | | | B-B1 | 27 |
| 28 | | | 30 mM | | | | 0.1 g/L | | | | B | 28 |
| 29 | | | | 30 mM M | | | 0.1 g/L | | | | E | 29 |
| 30 | 30 mM | | | | 5 g/L | 5 g/L | | | | | E | 30 |
| 31 | | 30 mM | | | 5 g/L | 5 g/L | | | | | D | 31 |
| 32 | | | 30 mM | | 5 g/L | 5 g/L | | | | | B1-C | 32 |
| 33 | | | | 30 mM M | 5 g/L | 5 g/L | | | | | C/D | 33 |
| 34 | 30 mM | | | | 5 g/L | | 0.1 g/L | | | | E2 (rest B) | 34 |
| 35 | | 30 mM | | | 5 g/L | | 0.1 g/L | | | | E | 35 |
| 36 | | | 30 mM | | 5 g/L | | 0.1 g/L | | | | E | 36 |
| 37 | | | | 30 mM M | 5 g/L | | 0.1 g/L | | | | B | 37 |
| 38 | 30 mM | | | | 5 g/L | 5 g/L | 0.1 g/L | | | | B | 38 |
| 39 | | 30 mM | | | 5 g/L | 5 g/L | 0.1 g/L | | | | B | 39 |
| 40 | | | 30 mM | | 5 g/L | 5 g/L | 0.1 g/L | | | | B | 40 |
| 41 | | | | 30 mM M | 5 g/L | 5 g/L | 0.1 g/L | | | | A | 41 |
| 42 | | | | | 5 g/L | | | | | | D | 42 |
| 43 | | | | | | | | 5 g/L | | | D | 43 |
| 44 | | | | | | | | | 5 g/L | | E1 | 44 |
| 45 | | | | | | | | | | 5 g/L | E1 | 45 |
| 46 | | | | | 5 g/L | 5 g/L | | | | | D | 46 |
| 47 | | | | | | 5 g/L | | 5 g/L | | | D | 47 |
| 48 | | | | | | 5 g/L | | | 5 g/L | | D-E | 48 |
| 49 | | | | | | 5 g/L | | | | 5 g/L | E | 49 |
| 50 | | | | | 5 g/L | | 0.1 g/L | | | | B1 | 50 |
| 51 | | | | | | | 0.1 g/L | 5 g/L | | | C-D | 51 |
| 52 | | | | | | | 0.1 g/L | | 5 g/L | | B1 | 52 |
| 53 | | | | | | | 0.1 g/L | | | 5 g/L | B1 | 53 |

As shown above, Trehalose provided the best results (i.e., the least amount of aggregation).

Example 3

Lyophilization Experiments

Lyophilization experiments were designed to assess the ability o various formulations to allow the formation of a lyo-cake which dissolves in less than 10 minutes and results in a clear solution. An accelerated stability study was also performed to demonstrate that no significant loss of biological activity.

The formulations shown in Table 6 below were lyophilized with a nitrogen lyophilizer TS20002 according to the manufacturer's instructions. The total time for lyophilization was approximately 72 hours. Each of the formulations below also contained 20 g/L Mannitol and 0.1 g/L TWEEN-80®.

TABLE 6

| Lyo 26 | Citrate | HEPES | Glycine | Histidine | Acetate | Tris | Phosphate | Lysine | Histidine | Glycine | Trehalose | Raffinose |
|---|---|---|---|---|---|---|---|---|---|---|---|---|
| 1 | 15 mM | | | | | | | | | | 10 g/L | |
| 2 | 15 mM | | | | | | | 15 mM | | | 10 g/L | |
| 3 | 15 mM | | | | | | | | 15 mM | | 10 g/L | |
| 4 | 15 mM | | | | | | | | | 15 mM | 10 g/L | |
| 5 | 15 mM | | | | | | | 15 mM | | 15 mM | 10 g/L | |
| 6 | 15 mM | | | | | | | 30 mM | | | 10 g/L | |
| 7 | 15 mM | | | | | | | | | | | 10 g/L |
| 8 | 15 mM | | | | | | | | 15 mM | | | 10 g/L |
| 9 | | 15 mM | | | | | | | | | 10 g/L | |
| 10 | | 15 mM | | | | | | 15 mM | | | 10 g/L | |
| 11 | | 15 mM | | | | | | | 15 mM | | 10 g/L | |
| 12 | | 15 mM | | | | | | | | 15 mM | 10 g/L | |
| 13 | | 15 mM | | | | | | 15 mM | | 15 mM | 10 g/L | |
| 14 | | 15 mM | | | | | | 15 mM | | 15 mM | | 10 g/L |
| 15 | | | 15 mM | | | | | | | | 10 g/L | |
| 16 | | | 15 mM | | | | | | 15 mM | | 10 g/L | |
| 17 | | | | 15 mM | | | | | | | 10 g/L | |
| 18 | | | | 15 mM | | | | 15 mM | | | 10 g/L | |
| 19 | | | | | 15 mM | | | 15 mM | | 15 mM | 10 g/L | |
| 20 | | | | | | 15 mM | | 15 mM | | 15 mM | 10 g/L | |
| 21 | | | | | | | 15 mM | 15 mM | | 15 mM | 10 g/L | |

The results of the lyophilzation experiments are shown in Table 7 below.

TABLE 7

| Lyo 26 | Buffer | | | | | | | — | Excipents | — | — | — |
| | Citrate | HEPES | Glycine | Histidine | Acetate | Tris | Phosphate | Lysine | Histidine | Glycine | Trehalose | Raffinose |
|---|---|---|---|---|---|---|---|---|---|---|---|---|
| 1 | 15 mM | | | | | | | | | | 10 g/L | |
| 2 | 15 mM | | | | | | | 15 mM | | | 10 g/L | |
| 3 | 15 mM | | | | | | | | 15 mM | | 10 g/L | |
| 4 | 15 mM | | | | | | | | | 15 mM | 10 g/L | |
| 5 | 15 mM | | | | | | | 15 mM | | | 10 g/L | |
| 6 | 15 mM | | | | | | | 30 mM | | | 10 g/L | |
| 7 | 15 mM | | | | | | | | | | | 10 g/L |
| 8 | 15 mM | | | | | | | | 15 mM | | | 10 g/L |
| 9 | | 15 mM | | | | | | | | | 10 g/L | |
| 10 | | 15 mM | | | | | | 15 mM | | | 10 g/L | |
| 11 | | 15 mM | | | | | | | 15 mM | | 10 g/L | |
| 12 | | 15 mM | | | | | | | | 15 mM | 10 g/L | |
| 13 | | 15 mM | | | | | | 15 mM | | 15 mM | 10 g/L | |
| 14 | | 15 mM | | | | | | 15 mM | | 15 mM | | 10 g/L |
| 15 | | | 15 mM | | | | | | | | 10 g/L | |
| 16 | | | 15 mM | | | | | | 15 mM | | 10 g/L | |
| 17 | | | | 15 mM | | | | | | | 10 g/L | |
| 18 | | | | 15 mM | | | | 15 mM | | | 10 g/L | |
| 19 | | | | | 15 mM | | | 15 mM | | 15 mM | 10 g/L | |
| 20 | | | | | | 15 mM | | 15 mM | | 15 mM | 10 g/L | |
| 21 | | | | | | | 15 mM | 15 mM | | 15 mM | 10 g/L | |

As shown above, either a Citrate or HEPES buffer in combination with an amino acid provided the clearest solution.

In order to assess stability of the reconstituted lyophilized rVWF, VWF:Ag and VWF:RCo tests were performed. VWF:Ag corresponds to the amount of VWF which can be detected in an VWF-specific ELISA using polyclonal anti-VWF antibody, while VWF:RCo corresponds to the amount of VWF which causes agglutination of stabilized platelets in the presence of ristocetin. Samples were stored at 40° C. Assuming applicability of the Arrhenius equation, one month stability at 40° C. is equivalent to approximately one year at 4° C. The results of the stability experiments are shown in Table 8 and Table 9 below.

TABLE 8

| rVWF:Ag | Weeks at 40° | | | |
|---|---|---|---|---|
| formulation | 0 | 4 | 5 | 8 |
| 1 | 121.1 | 89.8 | 113.0 | 106.6 |
| 2 | 121.8 | 102.0 | 114.0 | 112.8 |
| 3 | 119.9 | 102.0 | 105.,0 | 112.7 |
| 4 | 117.3 | 100.0 | 108.0 | 114.4 |
| 5 | 121.2 | 98.2 | 117.0 | 114.9 |
| 6 | 123.8 | 96.6 | 107.0 | — |
| 7 | 135.2 | 96.6 | 112.0 | 112.4 |
| 8 | 130.6 | 82.2 | 108.0 | 115.7 |
| 9 | 112.0 | 89.5 | 109.0 | 107.0 |
| 10 | 122.4 | 87.1 | 106.0 | 107.7 |
| 11 | 119.3 | 97.5 | 115.0 | 114.2 |
| 12 | 124.2 | 109.0 | 109.0 | 103.4 |
| 13 | 110.2 | 92.3 | 106.0 | 112.4 |
| 14 | 108.9 | 107.0 | 103.0 | 109.0 |

TABLE 9

| rVWF:RCo | Weeks at 40° | | | |
|---|---|---|---|---|
| formulation | 0 | 4 | 5 | 8 |
| 1 | 86 | 102 | 97.0 | 93.0 |
| 2 | 84 | 97 | 88.0 | 89.0 |
| 3 | 85 | 100 | 87.0 | 93.0 |
| 4 | | 102 | 81.0 | 98.0 |
| 5 | 85 | 89 | 88.0 | 98.0 |
| 6 | 83 | 102 | 88.0 | |
| 7 | | 92 | 97.0 | 95.0 |
| 8 | 88 | 94 | 90.0 | 104.0 |
| 9 | 93 | 91 | 97.0 | 100.0 |
| 10 | 95 | 87 | 87.0 | 87.0 |
| 11 | 86 | 93 | 89.0 | 99.0 |
| 12 | 84 | 91 | 89.0 | 95.0 |
| 13 | 88 | 87 | 96.0 | 89.0 |
| 14 | 90 | 91 | 86.0 | 92.0 |

The standard deviation for the ELISA is in the range of 10-20%. The results above indicate that all of the formulations tested provide good stability over 8 weeks at 40° C.

Additional stability experiments were performed where different amino acids were used in the formulations (e.g., glycine, lysine or histidine at 15 mM or 20 m), and where the citrate buffer was varied (e.g., 15, 20 or 25 mM). As described above, stability of rVWF was monitored using the VWF:RCo activity assay. Even after 13 months no significant differences were observed for VWF:RCo activity values of rVWF stability samples stored at 40° C. the significance of the measurements were tested with a t-Test. The intermediate precision of the assay was determined by calculating the Coefficient of Variance. In all series of the stability data the CV was below 20% and met the validation criteria of a CV<20%. Based on the above, it can be concluded that rVWF is stable in all citrate buffer systems tested, independent of buffer molarity and amino acids added. rVWF remains stable for at least 13 months even when stored at 40° C. The potency determination using the VWF:RCo activity assay shows good intermediate precision with CV values below 20%.

Thus, in view of the data presented herein, a formulation was proposed for rVWF including 15 mM citrate (Na$_3$Citrate×2H$_2$O), 15 mM glycine, 10 g/L Trehalose, 20 g/L Mannitol, 0.1 g/L TWEEN-80®, pH 7.3.

Example 4

Long Term Stability
Accelerated and Long-Term Stability Testing

Studies were conducted to evaluate the stability of the rVWF final drug product (FDP) stored at both the recommended and elevated storage conditions. Data from the elevated storage conditions provides assurance that deviations in the temperature will not impact the quality of the rVWF FDP and will be used to extrapolate the acceptable expiry condition of the material in the absence of real-time, real-condition stability data.

The current specification is ≤3.0% residual moisture (as determined using the Karl Fischer Method). Lots rVWFF #4FC, rVWFF #5FC, rVWFF #6FC and rVWFF #7FC were released with moisture levels of 1.2%, 1.3%, 1.2%, and 1.5% respectively. Based on the past experience with other products with similar vial and stopper configurations, it is expected that any rVWF lots released with approximately 1.3% residual moisture will meet the specification limit of ≤3.0% at the end of the proposed shelf life (i.e. 24 months at the intended storage temperature of 5° C.±3° C.).

Long-term stability studies at the recommended storage condition (i.e. 5° C. 3° C.) and elevated temperatures (i.e. 40° C.±2° C.) were conducted with four rVWF FDP lots that have been manufactured. These studies have provided sufficient data to compare the stability behavior of the individual clinical lots.

The stability protocol, including a description of the stability-indicating assays and stability-acceptance criteria, can be found in Table 10 which also contains information related to the rVWF FDP lots evaluated in the stability studies.

TABLE 10

| Storage Conditions (° C.) | Batch Number | Completed (and Proposed) Test Intervals |
|---|---|---|
| 5° C. ± 3° C. | rVWF#1FC | 0, 1, 2, 3, 6, 9, 12, 18, 24 months |
| 30° C. | rVWF#1FC | 0, 1, 3, 6 months |
| 5° C. ± 3° C. | rVWF#2FC | 0, 1, 2, 3, 6, months |
| 5° C. ± 3° C. | rVWF#3FC | 0, 1, 2, 3, 6, 9, 12, 18, 24 months |
| 30° C. | rVWF#3FC | 0, 0.5, 1, 2, 3, 6 months |
| 40° C. | rVWF#3FC | 0, 0.5, 1, 2, 3 months |
| 5° C. ± 3° C. | rVWF#4FC | 0, 1, 2, 3, 6, 9, 12, 18, 24, (30) months |
| 40° C. | rVWF#4FC | 0, 1, 2, 3, 6, 9 months |
| 5° C. ± 3° C. | rVWF#5FC | 0, 1, 2, 3, 6, 9, 12, 18, (24, 30) months |
| 40° C. | rVWF#5FC | 0, 1, 2, 3 6, 9 months |
| 5° C. ± 3° C. | rVWF#6FC | 0, 1, 2, 3, 6, 9, 12, (18, 24, 30) months |

TABLE 10-continued

| Storage Conditions (° C.) | Batch Number | Completed (and Proposed) Test Intervals |
|---|---|---|
| 40° C. | rVWF#6FC | 0, 1, 2, 3, 6, 9 months |
| 5° C. ± 3° C. | rVWF#7FC | 0, 1, 2, 3, 6, 9, 12, (18, 24, 30) months |
| 40° C. | rVWF#7FC | 0, 1, 2, 3, 6, 9 months |

Summary and Discussion of Overall Stability (24 Months)

The rVWF FDP stability data presented is comprised of the following:

1. 24 months data of long-term studies at 5° C.±3° C. (complete testing) and 6 months intermediate data at 30° C.±2° C. (complete testing) for lot rVWF #1FC;
2. 6 months data at 5° C.±3° C. (complete testing) for lot rVWF #2FC;
3. 24 months data of long-term studies at 2-8° (complete testing), 6 months data at 30° C.±2° C. and 3 months data at 40° C.±2° C. (complete testing) for lot rVWF #3FC;
4. 24 months stability data at 5° C.±3° C. and 9 months data at 40° C.±2° C. for lot rVWFF #4FC;
5. 24 months stability data at 5° C.±3° C. and 9 months data at 40° C.±2° C. for lot rVWFF #5FC;
6. 12 months stability data at 5° C.±3° C. and 9 months data at 40° C.±2° C. for lot rVWFF #6FC; and
7. 12 months stability data at 5° C.±3° C. and 9 months data at 40° C.±2° C. for lot rVWFF #7FC The variation observed in residual moisture for lots rVWFF #4FC, rVWFF #5FC, rVWFF #6FC and rVWFF #7FC has remained well below the acceptance criterion≤3%, and has not impacted the functional activity (VWF:RCo). There was no observable change in the stability results for qualitative analytical techniques (i.e. appearance, SDS-PAGE analysis, etc.) for the lots manufactured to be suitable for use in the non-clinical and clinical studies. Similarly, there was no trend in decreasing stability for the total protein analysis, the VWF:Ag analysis or the observed number of VWF multimers during storage.

Variation in both the ratio of VWF:RCo activity to VWF:Ag activity and the VWF:RCo data presented for lots rVWF #1FC, rVWF #2FC and rVWF #3FC was likely the result of variation of the test method, the fact that the individual VWF:RCo stability test results consisted of data from a single determination of one stability sample, and/or data from the non-Ph. Eur.-conforming method assay methodology. All testing time points for the non-clinical lots subsequent to the modification of the assay methodology to the Ph.Eur.-conforming assay were tested using both the original and new assay methodology.

The rVWF FDP manufactured at a large-scale exhibited similar stability characteristics to the rVWF FDP lots manufactured at an experimental scale. These rVWF FDP lots maintained VWF:RCo activity for up to 24 months of storage at 5° C.±3° C. There was no change in the VWF multimer pattern in samples of the large-scale lots currently on stability, even after 6 months of storage at 30° C.±2° C. or 9 months storage at 40° C.±2° C. Table 11 shows results for VWF:RCo, VWF:Ag and VWF multimer pattern of the batches rVWF #4FC, rVWF #5FC, rVWF #6FC and rVWF #7FC stored under stress condition at 40° C.±2° C. The results indicate stability at elevated temperature storage conditions for 9 months which can be extrapolated into a shelf life of more than 3 years at ambient temperatures or even more under refrigerated conditions.

TABLE 11

| Attribute | Specification | 0 | 1 | 2 | 3 | 6 | 9 |
|---|---|---|---|---|---|---|---|
| | | Results at Time (Months) | | | | | |
| Stability Data for rVWF#4FC at 40° C. ± 2° C. | | | | | | | |
| VWF:RCo Activity [U/ml][1] | 70-150 | 130 | 117 | 118 | 127 | 132 | 142 |
| VWF:Ag ELISA (U/ml) | Report result | 86 | 87 | 79 | 81 | 79 | 86 |
| VWF multimer analysis | Report result | 21 | 20 | 20 | 20 | 21 | 18 |
| Stability Data for rVWF#5FC at 40° C. ± 2° C. | | | | | | | |
| VWF:RCo Activity [U/ml][1] | 70-150 | 107 | 119 | 120 | 116 | 132 | 134 |
| VWF:Ag ELISA (U/ml) | Report result | 94 | 86 | 84 | 91 | 90 | 79 |
| VWF multimer analysis | Report result | 20 | 20 | 18 | 19 | 20 | 19 |
| Stability Data for rVWF#6FC at 40° C. ± 2° C. | | | | | | | |
| VWF:RCo Activity [U/ml][1] | 70-150 | 118 | 111 | 126 | 129 | 130 | 119 |
| VWF:Ag ELISA (U/ml) | Report result | 85 | 95 | 86.3 | 73.5 | 80.8 | 70.3 |
| VWF multimer analysis | Report result | 20 | 19 | 20 | 20 | 20 | n.t. |
| Stability Data for rVWF#7FC at 40° C. ± 2° C. | | | | | | | |
| VWF:RCo Activity [U/ml][1] | 70-150 | 111 | 115 | 122 | 105 | 99 | 112 |
| VWF:Ag ELISA (U/ml) | Report result | 87.3 | 85.3 | 77.5 | 68.8 | 75 | 73.8 |
| VWF multimer analysis | Report result | 21 | 20 | 20 | 19 | 19 | 19 |

An analysis of covariance (ANCOVA analysis) demonstrated that the difference in slopes of the regression lines (lots rVWFF #4FC, rVWFF #5FC, rVWFF #6FC and rVWFF #7FC stored at 5° C. 3° C.) is not significant (p=0.906), allowing the VWF:RCo activity data to be pooled as described in ICH Q1A (R2). The difference in elevation of the trend lines of the individual lots is also not significant. Extrapolation of the pooled worse case slope, as shown in FIG. 1, shows that the confidence intervals are well within the acceptance criteria for a minimum of 24 months. The lower confidence interval for the mean curve decreases to 80% of initial activity at 51 months (80% is also the maximum difference between estimated potency and stated potency for Human von Willebrand Factor in Ph.Eur). The pooled worse case slope shows a decrease of 0.0344 U VWF:RCo per month. This comparison shows that stability characteristics of the rVWF FDP, specifically the VWF:RCo activity, did not change as a result of the changes in the production process. The above extrapolation supports the extension of the provisional shelf life of rVWF FDP to 24 months when stored at the recommended storage temperature.

Figure 2:
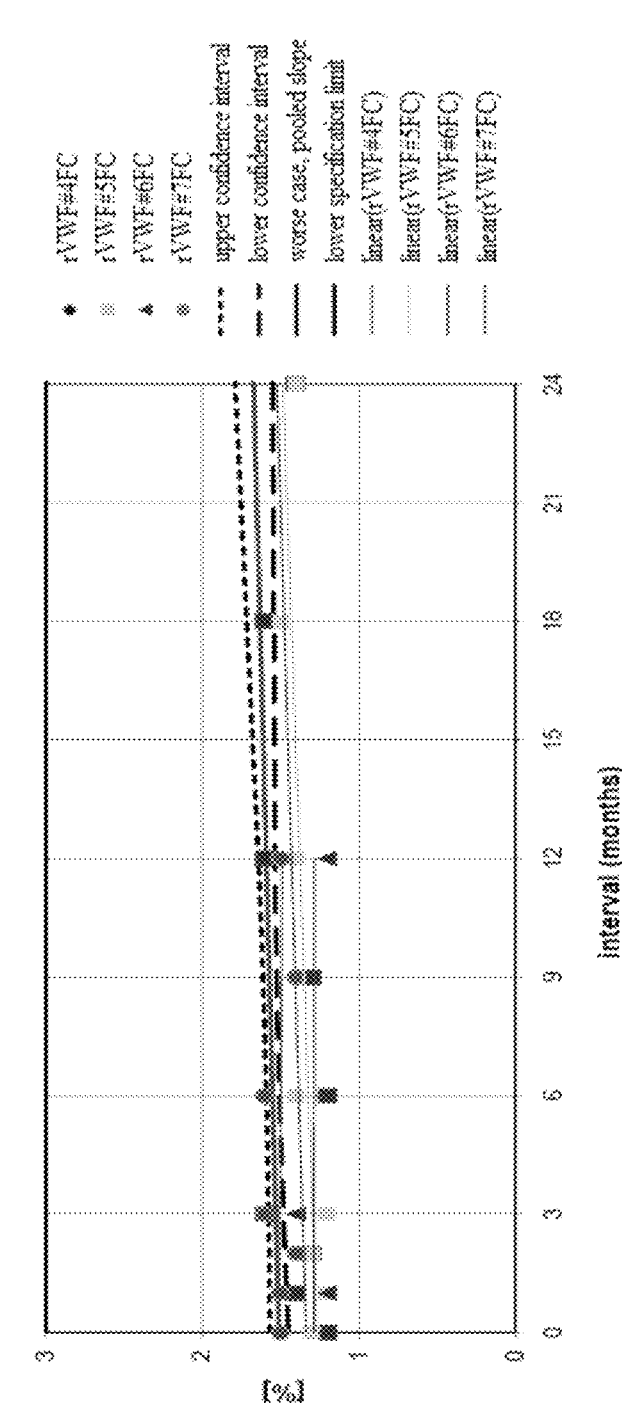
FIG. 2 shows the increase in residual moisture in rVWF FDP stored at 5° C. 3° C.
Figure 3:
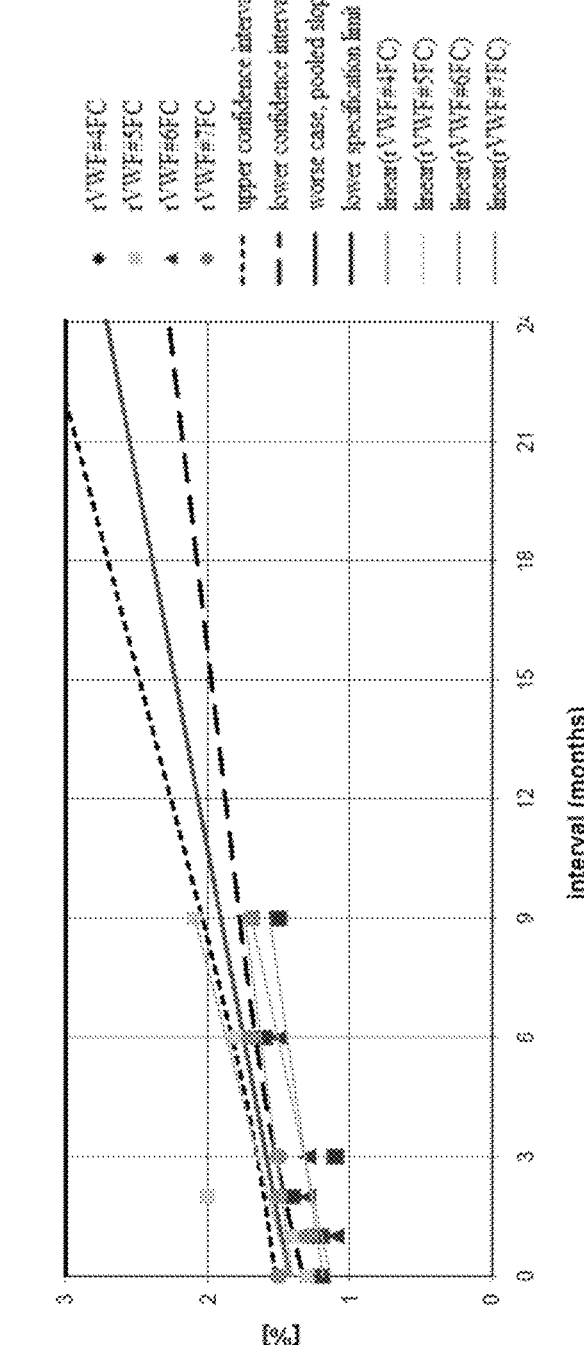
FIG. 3 shows the increase in residual moisture in rVWF FDP stored at 40° C. 2° C.

The transfer of moisture from the stopper to the lyophilized product is dependent on the stopper material and is influenced by the residual moisture of the stopper after sterilization, the humidity at which the sample is stored and the intrinsic moisture transfer rate of the stopper. The residual moisture in the lots rVWFF #4FC, rVWFF #5FC, rVWFF #6FC and rVWFF #7FC stored at 5° C.±3° C. was comparable (the difference in comparison of slopes being not significant, with p=0.734), as shown in FIG. 2. Lots stored at the elevated temperature condition 40° C.±2° C. also showed a comparable increase in residual moisture over 9 months (FIG. 3). ANCOVA analysis demonstrates here that the difference in slope of the regression lines is comparable (p=0.546). FIG. 3 shows the extrapolation of the worse case pooled slope up to 24 months.

These are sufficient data to support the use of lots rVWFF #6FC and rVWFF #7FC for the duration of the described expiry period of 24 months when stored at 5° C.±3° C.

Proposed Storage Conditions and Shelf Life

The recommended storage condition for the rVWF FDP is 5° C.±3° C. A provisional shelf life of 24 months for the rVWF FDP is therefore proposed when stored at the recommended storage condition. The shelf life for the rVWF FDP lots likely can be further extended based on additional data to be generated for longer storage periods.

---

What is claimed is:

1. A method of preparing a stable lyophilized pharmaceutical formulation of a recombinant von Willebrand Factor (rVWF) wherein the method comprises:

(a) adding a buffer, one or more amino acids, one or more stabilizing agents, and one or more surfactants to a rVWF to obtain a solution; and (b) lyophilizing said solution from step (a);

wherein said rVWF comprises a polypeptide selected from the group consisting of:

i) the amino acid sequence set out in SEQ ID NO: 3; and ii) a biologically active fragment comprising the region of SEQ ID NO:3 from Val449 to Asn730 which causes agglutination of stabilized platelets in the presence of ristocetin, which has the activity to stabilize Factor VIII, or which binds to glycoprotein 1b (GP1b), collagen or heparin;

wherein said buffer comprises a pH buffering agent selected from the group consisting of citrate and HEPES at 15 mM and said pH is in a range of about 2.0 to about 12.0;

wherein said one or more amino acids is selected from the group consisting of glycine, lysine, and histidine at a concentration of about 1 to about 500 mM;

wherein said one or more stabilizing agents is at a concentration of about 0.1 to about 1000 mM and is selected from the group consisting of mannitol, lactose, sorbitol, xylitol, sucrose, trehalose, mannose, maltose, glucose, raffinose, cellobiose, gentiobiose, isomaltose, arabinose, glucosamine, fructose and combinations of these stabilizing agents; and wherein said one or more surfactants is at a concentration of about 0.01 g/L to about 0.5 g/L.

2. The method of claim 1 wherein the buffering agent is citrate.

3. The method of claim 1 wherein pH is in the range of about 6.0 to about 8.0.

4. The method of claim 3 wherein pH is in the range of about 6.5 to about 7.5.

5. The method of claim 1 wherein pH is about 7.3.

6. The method of claim 1 wherein the buffering agent is a citrate buffer and the pH is about 7.3.

7. The method of claim 1 wherein the one or more amino acids is at a concentration range of about 0.5 mM to about 300 mM.

8. The method of claim 7 wherein the one or more amino acids is glycine at a concentration of about 15 mM.

9. The method of claim 1 wherein the rVWF comprises the amino acid sequence set out in SEQ ID NO: 3, or the biologically active fragment comprising the region of SEQ ID NO:3 from Val449 to Asn730 which causes agglutination of stabilized platelets in the presence of ristocetin, or binds to Factor VIII; wherein the buffering agent is a citrate buffer and the pH is about 7.3; and wherein the one or more amino acids is glycine at a concentration of about 15 mM.

10. The method of claim 1 wherein the one or more stabilizing agents are trehalose at a concentration of about 10 g/L and mannitol at a concentration of about 20 g/L.

11. The method of claim 1 wherein the surfactant is selected from the group consisting of digitonin, 2-[4-(2,4,4-trimethylpentan-2-yl)phenoxy]ethanol, p-(1,1,3,3-tetramethylbutyl)phenyl-polyethylene glycol, polysorbate 20, polysorbate 80 and combinations of these surfactants.

12. The method of claim 11 wherein the one or more surfactants is polysorbate 80 at about 0.01 g/L.

13. The method of claim 1 wherein the rVWF comprises the amino acid sequence set out in SEQ ID NO: 3, or the biologically active fragment comprising the region of SEQ ID NO:3 from Val449 to Asn730; wherein the buffering agent is a citrate buffer at a concentration of about 15 mM and the pH is about 7.3; wherein the one or more amino acids is glycine at a concentration of about 15 mM; wherein the one or more stabilizing agents are trehalose at a concentration of about 10 g/L and mannitol at a concentration of about 20 g/L; and wherein the one or more surfactants is polyoxyethylene (80) sorbitan monooleate at about 0.1 g/L.

14. The method of claim 1 wherein an amount of VWF which causes agglutination of stabilized platelets in the presence of ristocetin (VWF:RCo) in the lyophilized pharmaceutical formulation after reconstitution is from 83 U/ml to 142 U/ml.

15. The method of claim 1 wherein the lyophilized pharmaceutical formulation after reconstitution maintains VWF:RCo activity for up to 24 months of storage at 5° C.±3° C.

16. The method of claim 1 wherein VWF:RCo activity of the lyophilized pharmaceutical formulation after reconstitution is characterized with no more than a decrease of 0.0344 U/ml VWF:RCo per month.

\* \* \* \* \*